US008846895B2

(12) United States Patent
Du et al.

(10) Patent No.: US 8,846,895 B2
(45) Date of Patent: Sep. 30, 2014

(54) DOUBLE-STRANDED RNA MOLECULES WITH STABILITY IN MAMMALIAN BODY FLUID, PREPARATION AND APPLICATION THEREOF

(75) Inventors: Quan Du, Beijing (CN); Zicai Liang, Beijing (CN)

(73) Assignee: Biomics Biotechnologies Co. Ltd. (CN)

( * ) Notice: Subject to any disclaimer, the term of this patent is extended or adjusted under 35 U.S.C. 154(b) by 0 days.

(21) Appl. No.: 13/582,936

(22) PCT Filed: Mar. 29, 2011

(86) PCT No.: PCT/CN2011/000536

§ 371 (c)(1), (2), (4) Date: Oct. 2, 2012

(87) PCT Pub. No.: WO2011/120332

PCT Pub. Date: Oct. 6, 2011

(65) Prior Publication Data

US 2013/0065940 A1 Mar. 14, 2013

(30) Foreign Application Priority Data

Mar. 29, 2010 (CN) .......................... 2010 1 0134253

(51) Int. Cl.

*C07H 21/04* (2006.01)
*C07H 21/02* (2006.01)
*C12Q 1/68* (2006.01)
*A61K 48/00* (2006.01)

(52) U.S. Cl.

USPC ................ 536/24.5; 536/23.1; 435/6; 514/44

(58) Field of Classification Search

None

See application file for complete search history.

(56) References Cited

PUBLICATIONS

Volkov et al., Oligonucleotides, vol. 19, No. 2, 2009.*

* cited by examiner

*Primary Examiner* — Amy Bowman

(74) *Attorney, Agent, or Firm* — Fox Rothschild LLP; Jianming Jimmy Hao

(57) ABSTRACT

The present invention discloses preparation and application of double-stranded RNA molecules stable in mammalian body fluids. The mammalian-body-fluid-stable RNA molecules disclosed in the present invention are comprised of only unmodified nucleotides. For the first time, the present invention discloses the applications of mammalian-body-fluid-stable RNA molecules for immunotherapy and siRNA drug development.

18 Claims, 1 Drawing Sheet

In vivo stability assay of siRNAs
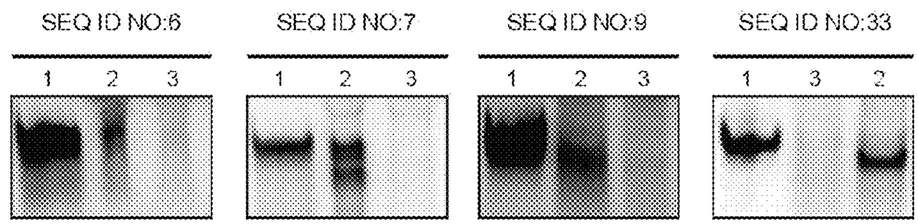

SEQUENCE LISTING

```
<160> NUMBER OF SEQ ID NOS: 54

<210> SEQ ID NO 1
<211> LENGTH: 1653
<212> TYPE: DNA
<213> ORGANISM: Photinus pyralis

<400> SEQUENCE: 1

atggaagacg ccaaaaacat aaagaaaggc ccggcgccat tctatccgct ggaagatgga     60

accgctggag agcaactgca taaggctatg aagagatacg ccctggttcc tggaacaatt    120

gcttttacag atgcacatat cgaggtggac atcacttacg ctgagtactt cgaaatgtcc    180

gttcggttgg cagaagctat gaaacgatat gggctgaata caaatcacag aatcgtcgta    240

tgcagtgaaa actctcttca attctttatg ccggtgttgg gcgcgttatt tatcggagtt    300

gcagttgcgc ccgcgaacga catttataat gaacgtgaat tgctcaacag tatgggcatt    360

tcgcagccta ccgtggtgtt cgtttccaaa aaggggttgc aaaaaatttt gaacgtgcaa    420

aaaaagctcc caatcatcca aaaaattatt atcatggatt ctaaaacgga ttaccaggga    480

tttcagtcga tgtacacgtt cgtcacatct catctacctc ccggttttaa tgaatacgat    540

tttgtgccag agtccttcga tagggacaag acaattgcac tgatcatgaa ctcctctgga    600

tctactggtc tgcctaaagg tgtcgctctg cctcatagaa ctgcctgcgt gagattctcg    660

catgccagag atcctatttt tggcaatcaa atcattccgg atactgcgat tttaagtgtt    720

gttccattcc atcacggttt tggaatgttt actacactcg gatatttgat atgtggattt    780

cgagtcgtct taatgtatag atttgaagaa gagctgtttc tgaggagcct tcaggattac    840

aagattcaaa gtgcgctgct ggtgccaacc ctattctcct tcttcgccaa aagcactctg    900

attgacaaat acgatttatc taatttacac gaaattgctt ctggtggcgc tcccctctct    960

aaggaagtcg gggaagcggt tgccaagagg ttccatctgc caggtatcag gcaaggatat   1020

gggctcactg agactacatc agctattctg attacacccg agggggatga taaaccgggc   1080

gcggtcggta aagttgttcc atttttttgaa gcgaaggttg tggatctgga taccgggaaa  1140

acgctgggcg ttaatcaaag aggcgaactg tgtgtgagag gtcctatgat tatgtccggt   1200

tatgtaaaca atccggaagc gaccaacgcc ttgattgaca aggatggatg gctacattct   1260

ggagacatag cttactggga cgaagacgaa cacttcttca tcgttgaccg cctgaagtct   1320

ctgattaagt acaaaggcta tcaggtggct cccgctgaat tggaatccat cttgctccaa   1380

caccccaaca tcttcgacgc aggtgtcgca ggtcttcccg acgatgacgc cggtgaactt   1440

cccgccgccg ttgttgtttt ggagcacgga aagacgatga cggaaaaaga gatcgtggat   1500

tacgtcgcca gtcaagtaac aaccgcgaaa aagttgcgcg gaggagttgt gtttgtggac   1560

gaagtaccga aaggtcttac cggaaaactc gacgcaagaa aaatcagaga gatcctcata   1620

aaggccaaga agggcggaaa gatcgccgtg taa                                1653

<210> SEQ ID NO 2
```

<211> LENGTH: 2586
<212> TYPE: DNA
<213> ORGANISM: Homo sapiens

<400> SEQUENCE: 2

```
gattggggtt ttcccctccc atgtgctcaa gactggcgct aaaagttttg agcttctcaa     60
aagtctagag ccaccgtcca gggagcaggt agctgctggg ctccggggac actttgcgtt    120
cgggctggga gcgtgctttc cacgacggtg acacgcttcc ctggattggc agccagactg    180
ccttccgggt cactgccatg gaggagccgc agtcagatcc tagcgtcgag ccccctctga    240
gtcaggaaac attttcagac ctatggaaac tacttcctga aaacaacgtt ctgtccccct    300
tgccgtccca agcaatggat gatttgatgc tgtccccgga cgatattgaa caatggttca    360
ctgaagaccc aggtccagat gaagctccca gaatgccaga ggctgctccc cccgtggccc    420
ctgcaccagc agctcctaca ccggcggccc ctgcaccagc cccctcctgg cccctgtcat    480
cttctgtccc ttcccagaaa acctaccagg gcagctacgg tttccgtctg ggcttcttgc    540
attctgggac agccaagtct gtgacttgca cgtactcccc tgccctcaac aagatgtttt    600
gccaactggc caagacctgc cctgtgcagc tgtgggttga ttccacaccc ccgcccggca    660
cccgcgtccg cgccatggcc atctacaagc agtcacagca catgacggag gttgtgaggc    720
gctgccccca ccatgagcgc tgctcagata gcgatggtct ggcccctcct cagcatctta    780
tccgagtgga aggaaatttg cgtgtggagt atttggatga cagaaacact tttcgacata    840
gtgtggtggt gccctatgag ccgcctgagg ttggctctga ctgtaccacc atccactaca    900
actacatgtg taacagttcc tgcatgggcg gcatgaaccg gaggcccatc ctcaccatca    960
tcacactgga agactccagt ggtaatctac tgggacggaa cagctttgag gtgcgtgttt   1020
gtgcctgtcc tgggagagac cggcgcacag aggaagagaa tctccgcaag aaaggggagc   1080
ctcaccacga gctgccccca gggagcacta agcgagcact gcccaacaac accagctcct   1140
ctccccagcc aaagaagaaa ccactggatg gagaatattt caccctcag atccgtgggc    1200
gtgagcgctt cgagatgttc cgagagctga atgaggcctt ggaactcaag gatgcccagg   1260
ctgggaagga gccagggggg agcagggctc actccagcca cctgaagtcc aaaaagggtc   1320
agtctacctc ccgccataaa aaactcatgt tcaagacaga agggcctgac tcagactgac   1380
attctccact tcttgttccc cactgacagc ctcccacccc catctctccc tcccctgcca   1440
ttttgggttt tgggtctttg aacccttgct tgcaataggt gtgcgtcaga agcacccagg   1500
acttccattt gctttgtccc ggggctccac tgaacaagtt ggcctgcact ggtgttttgt   1560
tgtggggagg aggatgggga gtaggacata ccagcttaga ttttaaggtt tttactgtga   1620
gggatgtttg ggagatgtaa gaaatgttct tgcagttaag ggttagttta caatcagcca   1680
cattctaggt aggggcccac ttcaccgtac taaccaggga agctgtccct cactgttgaa   1740
ttttctctaa cttcaaggcc catatctgtg aaatgctggc atttgcacct acctcacaga   1800
gtgcattgtg agggttaatg aaataatgta catctggcct tgaaaccacc ttttattaca   1860
tggggtctag aacttgaccc ccttgagggt gcttgttccc tctccctgtt ggtcggtggg   1920
ttggtagttt ctacagttgg gcagctggtt aggtagaggg agttgtcaag tctctgctgg   1980
cccagccaaa ccctgtctga caacctcttg gtgaacctta gtacctaaaa ggaaatctca   2040
ccccatccca caccctggag gatttcatct cttgtatatg atgatctgga tccaccaaga   2100
cttgttttat gctcagggtc aatttctttt ttcttttttt tttttttttt tctttttctt   2160
tgagactggg tctcgctttg ttgcccaggc tggagtggag tggcgtgatc ttggcttact   2220
```

```
gcagcctttg cctccccggc tcgagcagtc ctgcctcagc ctccggagta gctgggacca   2280

caggttcatg ccaccatggc cagccaactt ttgcatgttt tgtagagatg gggtctcaca   2340

gtgttgccca ggctggtctc aaactcctgg gctcaggcga tccacctgtc tcagcctccc   2400

agagtgctgg gattacaatt gtgagccacc acgtccagct ggaagggtca acatctttta   2460

cattctgcaa gcacatctgc attttcaccc caccccttccc ctccttctcc ctttttatat  2520

cccattttta tatcgatctc ttattttaca ataaaacttt gctgccacct gtgtgtctga   2580

ggggtg                                                               2586

<210> SEQ ID NO 3
<211> LENGTH: 7224
<212> TYPE: DNA
<213> ORGANISM: Homo sapiens

<400> SEQUENCE: 3

gtaccttgat ttcgtattct gagaggctgc tgcttagcgg tagccccttg gtttccgtgg     60

caacggaaaa gcgcgggaat tacagataaa ttaaaactgc gactgcgcgg cgtgagctcg    120

ctgagacttc ctggacgggg gacaggctgt ggggtttctc agataactgg gcccctgcgc    180

tcaggaggcc ttcaccctct gctctgggta aagttcattg gaacagaaag aaatggattt    240

atctgctctt cgcgttgaag aagtacaaaa tgtcattaat gctatgcaga aaatcttaga    300

gtgtcccatc tgtctggagt tgatcaagga acctgtctcc acaaagtgtg accacatatt    360

ttgcaaattt tgcatgctga aacttctcaa ccagaagaaa gggccttcac agtgtccttt    420

atgtaagaat gatataacca aaaggagcct acaagaaagt acgagattta gtcaacttgt    480

tgaagagcta ttgaaaatca tttgtgcttt tcagcttgac acaggtttgg agtatgcaaa    540

cagctataat tttgcaaaaa aggaaaataa ctctcctgaa catctaaaag atgaagtttc    600

tatcatccaa agtatgggct acagaaaccg tgccaaaaga cttctacaga gtgaacccga    660

aaatccttcc ttgcaggaaa ccagtctcag tgtccaactc tctaaccttg gaactgtgag    720

aactctgagg acaaagcagc ggatacaacc tcaaaagacg tctgtctaca ttgaattggg    780

atctgattct tctgaagata ccgttaataa ggcaacttat tgcagtgtgg gagatcaaga    840

attgttacaa atcacccctc aaggaaccag ggatgaaatc agtttggatt ctgcaaaaaa    900

ggctgcttgt gaattttctg agacggatgt aacaaatact gaacatcatc aacccagtaa    960

taatgatttg aacaccactg agaagcgtgc agctgagagg catccagaaa agtatcaggg   1020

tagttctgtt tcaaacttgc atgtggagcc atgtggcaca aatactcatg ccagctcatt   1080

acagcatgag aacagcagtt tattactcac taaagacaga atgaatgtag aaaaggctga   1140

attctgtaat aaaagcaaac agcctggctt agcaaggagc caacataaca gatgggctgg   1200

aagtaaggaa acatgtaatg ataggcggac tcccagcaca gaaaaaaagg tagatctgaa   1260

tgctgatccc ctgtgtgaga gaaaagaatg gaataagcag aaactgccat gctcagagaa   1320

tcctagagat actgaagatg ttccttggat aacactaaat agcagcattc agaaagttaa   1380

tgagtggttt tccagaagtg atgaactgtt aggttctgat gactcacatg atggggagtc   1440

tgaatcaaat gccaaagtag ctgatgtatt ggacgttcta aatgaggtag atgaatattc   1500

tggttcttca gagaaaatag acttactggc cagtgatcct catgaggctt taatatgtaa   1560

aagtgaaaga gttcactcca aatcagtaga gagtaatatt gaagacaaaa tatttgggaa   1620

aacctatcgg aagaaggcaa gcctccccaa cttaagccat gtaactgaaa atctaattat   1680
```

```
aggagcattt gttactgagc cacagataat acaagagcgt cccctcacaa ataaattaaa   1740

gcgtaaaagg agacctacat caggccttca tcctgaggat tttatcaaga aagcagattt   1800

ggcagttcaa aagactcctg aaatgataaa tcagggaact aaccaaacgg agcagaatgg   1860

tcaagtgatg aatattacta atagtggtca tgagaataaa acaaaaggtg attctattca   1920

gaatgagaaa aatcctaacc caatagaatc actcgaaaaa gaatctgctt tcaaaacgaa   1980

agctgaacct ataagcagca gtataagcaa tatggaactc gaattaaata tccacaattc   2040

aaaagcacct aaaaagaata ggctgaggag gaagtcttct accaggcata ttcatgcgct   2100

tgaactagta gtcagtagaa atctaagccc acctaattgt actgaattgc aaattgatag   2160

ttgttctagc agtgaagaga taaagaaaaa aaagtacaac caaatgccag tcaggcacag   2220

cagaaaccta caactcatgg aaggtaaaga acctgcaact ggagccaaga agagtaacaa   2280

gccaaatgaa cagacaagta aaagacatga cagcgatact ttcccagagc tgaagttaac   2340

aaatgcacct ggttctttta ctaagtgttc aaataccagt gaacttaaag aatttgtcaa   2400

tcctagcctt ccaagagaag aaaaagaaga gaaactagaa acagttaaag tgtctaataa   2460

tgctgaagac cccaaagatc tcatgttaag tggagaaagg gttttgcaaa ctgaaagatc   2520

tgtagagagt agcagtattt cattggtacc tggtactgat tatggcactc aggaaagtat   2580

ctcgttactg gaagttagca ctctagggaa ggcaaaaaca gaaccaaata aatgtgtgag   2640

tcagtgtgca gcatttgaaa accccaaggg actaattcat ggttgttcca aagataatag   2700

aaatgacaca gaaggcttta agtatccatt gggacatgaa gttaaccaca gtcgggaaac   2760

aagcatagaa atggaagaaa gtgaacttga tgctcagtat ttgcagaata cattcaaggt   2820

ttcaaagcgc cagtcatttg ctccgttttc aaatccagga aatgcagaag aggaatgtgc   2880

aacattctct gcccactctg ggtccttaaa gaaacaaagt ccaaaagtca cttttgaatg   2940

tgaacaaaag gaagaaaatc aaggaaagaa tgagtctaat atcaagcctg tacagacagt   3000

taatatcact gcaggctttc ctgtggttgg tcagaaagat aagccagttg ataatgccaa   3060

atgtagtatc aaaggaggct ctaggttttg tctatcatct cagttcagag gcaacgaaac   3120

tggactcatt actccaaata aacatggact tttacaaaac ccatatcgta taccaccact   3180

ttttcccatc aagtcatttg ttaaaactaa atgtaagaaa aatctgctag aggaaaactt   3240

tgaggaacat tcaatgtcac ctgaaagaga aatgggaaat gagaacattc caagtacagt   3300

gagcacaatt agccgtaata acattagaga aaatgttttt aaagaagcca gctcaagcaa   3360

tattaatgaa gtaggttcca gtactaatga agtgggctcc agtattaatg aaataggttc   3420

cagtgatgaa aacattcaag cagaactagg tagaaacaga gggccaaaat tgaatgctat   3480

gcttagatta ggggttttgc aacctgaggt ctataaacaa agtcttcctg gaagtaattg   3540

taagcatcct gaaataaaaa agcaagaata tgaagaagta gttcagactg ttaatacaga   3600

tttctctcca tatctgattt cagataactt agaacagcct atgggaagta gtcatgcatc   3660

tcaggtttgt tctgagacac ctgatgacct gttagatgat ggtgaaataa aggaagatac   3720

tagttttgct gaaaatgaca ttaaggaaag ttctgctgtt tttagcaaaa gcgtccagaa   3780

aggagagctt agcaggagtc ctagcccttt cacccataca catttggctc agggttaccg   3840

aagaggggcc aagaaattag agtcctcaga agagaactta tctagtgagg atgaagagct   3900

tccctgcttc caacacttgt tatttggtaa agtaaacaat ataccttctc agtctactag   3960

gcatagcacc gttgctaccg agtgtctgtc taagaacaca gaggagaatt tattatcatt   4020

gaagaatagc ttaaatgact gcagtaacca ggtaatattg gcaaaggcat ctcaggaaca   4080
```

```
tcaccttagt gaggaaacaa aatgttctgc tagcttgttt tcttcacagt gcagtgaatt   4140
ggaagacttg actgcaaata caaacaccca ggatcctttc ttgattggtt cttccaaaca   4200
aatgaggcat cagtctgaaa gccagggagt tggtctgagt gacaaggaat tggtttcaga   4260
tgatgaagaa agaggaacgg gcttggaaga aaataatcaa gaagagcaaa gcatggattc   4320
aaacttaggt gaagcagcat ctgggtgtga gagtgaaaca agcgtctctg aagactgctc   4380
agggctatcc tctcagagtg acattttaac cactcagcag agggatacca tgcaacataa   4440
cctgataaag ctccagcagg aaatggctga actagaagct gtgttagaac agcatgggag   4500
ccagccttct aacagctacc cttccatcat aagtgactct tctgcccttg aggacctgcg   4560
aaatccagaa caaagcacat cagaaaaagc agtattaact tcacagaaaa gtagtgaata   4620
ccctataagc cagaatccag aaggcctttc tgctgacaag tttgaggtgt ctgcagatag   4680
ttctaccagt aaaaataaag aaccaggagt ggaaaggtca tccccttcta aatgcccatc   4740
attagatgat aggtggtaca tgcacagttg ctctgggagt cttcagaata gaaactaccc   4800
atctcaagag gagctcatta aggttgttga tgtggaggag caacagctgg aagagtctgg   4860
gccacacgat ttgacggaaa catcttactt gccaaggcaa gatctagagg gaacccctta   4920
cctggaatct ggaatcagcc tcttctctga tgaccctgaa tctgatcctt ctgaagacag   4980
agccccagag tcagctcgtg ttggcaacat accatcttca acctctgcat tgaaagttcc   5040
ccaattgaaa gttgcagaat ctgcccagag tccagctgct gctcatacta ctgatactgc   5100
tgggtataat gcaatggaag aaagtgtgag cagggagaag ccagaattga cagcttcaac   5160
agaaagggtc aacaaaagaa tgtccatggt ggtgtctggc ctgaccccag aagaatttat   5220
gctcgtgtac aagtttgcca gaaaacacca catcacttta actaatctaa ttactgaaga   5280
gactactcat gttgttatga aaacagatgc tgagtttgtg tgtgaacgga cactgaaata   5340
ttttctagga attgcgggag gaaaatgggt agttagctat ttctgggtga cccagtctat   5400
taaagaaaga aaaatgctga atgagcatga ttttgaagtc agaggagatg tggtcaatgg   5460
aagaaaccac caaggtccaa agcgagcaag agaatcccag gacagaaaga tcttcagggg   5520
gctagaaatc tgttgctatg ggcccttcac caacatgccc acagatcaac tggaatggat   5580
ggtacagctg tgtggtgctt ctgtggtgaa ggagctttca tcattcaccc ttggcacagg   5640
tgtccaccca attgtggttg tgcagccaga tgcctggaca gaggacaatg gcttccatgc   5700
aattgggcag atgtgtgagg cacctgtggt gacccgagag tgggtgttgg acagtgtagc   5760
actctaccag tgccaggagc tggacaccta cctgataccc cagatccccc acagccacta   5820
ctgactgcag ccagccacag gtacagagcc acaggacccc aagaatgagc ttacaaagtg   5880
gcctttccag gccctgggag ctcctctcac tcttcagtcc ttctactgtc ctggctacta   5940
aatattttat gtacatcagc ctgaaaagga cttctggcta tgcaagggtc ccttaaagat   6000
tttctgcttg aagtctccct tggaaatctg ccatgagcac aaaattatgg taatttttca   6060
cctgagaaga ttttaaaacc atttaaacgc caccaattga gcaagatgct gattcattat   6120
ttatcagccc tattctttct attcaggctg ttgttggctt agggctggaa gcacagagtg   6180
gcttggcctc aagagaatag ctggtttccc taagtttact tctctaaaac cctgtgttca   6240
caaaggcaga gagtcagacc cttcaatgga aggagagtgc ttgggatcga ttatgtgact   6300
taaagtcaga atagtccttg ggcagttctc aaatgttgga gtggaacatt ggggaggaaa   6360
ttctgaggca ggtattagaa atgaaaagga aacttgaaac ctgggcatgg tggctcacgc   6420
```

```
ctgtaatccc agcactttgg gaggccaagg tgggcagatc actggaggtc aggagttcga   6480

aaccagcctg gccaacatgg tgaaacccca tctctactaa aaatacagaa attagccggt   6540

catggtggtg gacacctgta atcccagcta ctcaggtggc taaggcagga gaatcacttc   6600

agcccgggag gtggaggttg cagtgagcca agatcatacc acggcactcc agcctgggtg   6660

acagtgagac tgtggctcaa aaaaaaaaaa aaaaaaagga aaatgaaact agaagagatt   6720

tctaaaagtc tgagatatat ttgctagatt tctaaagaat gtgttctaaa acagcagaag   6780

attttcaaga accggtttcc aaagacagtc ttctaattcc tcattagtaa taagtaaaat   6840

gtttattgtt gtagctctgg tatataatcc attcctctta aaatataaga cctctggcat   6900

gaatatttca tatctataaa atgacagatc ccaccaggaa ggaagctgtt gctttctttg   6960

aggtgatttt tttcctttgc tccctgttgc tgaaaccata cagcttcata aataattttg   7020

cttgctgaag gaagaaaaag tgtttttcat aaacccatta tccaggactg tttatagctg   7080

ttggaaggac taggtcttcc ctagcccccc cagtgtgcaa gggcagtgaa gacttgattg   7140

tacaaaatac gttttgtaaa tgttgtgctg ttaacactgc aaataaactt ggtagcaaac   7200

acttccaaaa aaaaaaaaaa aaaa                                          7224
```

<210> SEQ ID NO 4
<211> LENGTH: 6270
<212> TYPE: DNA
<213> ORGANISM: Homo sapiens

<400> SEQUENCE: 4

```
aggagctggc ggagggcgtt cgtcctggga ctgcacttgc tcccgtcggg tcgcccggct     60

tcaccggacc cgcaggctcc cggggcaggg ccggggccag agctcgcgtg tcggcgggac    120

atgcgctgcg tcgcctctaa cctcgggctg tgctcttttt ccaggtggcc cgccggtttc    180

tgagccttct gccctgcggg gacacggtct gcaccctgcc cgcggccacg gaccatgacc    240

atgaccctcc acaccaaagc atctgggatg gccctactgc atcagatcca agggaacgag    300

ctggagcccc tgaaccgtcc gcagctcaag atccccctgg agcggcccct gggcgaggtg    360

tacctggaca gcagcaagcc cgccgtgtac aactaccccg agggcgccgc ctacgagttc    420

aacgccgcgg ccgccgccaa cgcgcaggtc tacggtcaga ccggcctccc ctacggcccc    480

gggtctgagg ctgcggcgtt cggctccaac ggcctggggg gtttcccccc actcaacagc    540

gtgtctccga gcccgctgat gctactgcac ccgccgccgc agctgtcgcc tttcctgcag    600

ccccacggcc agcaggtgcc ctactacctg gagaacgagc ccagcggcta cacggtgcgc    660

gaggccggcc cgccggcatt ctacaggcca aattcagata atcgacgcca gggtggcaga    720

gaaagattgg ccagtaccaa tgacaaggga agtatggcta tggaatctgc caaggagact    780

cgctactgtg cagtgtgcaa tgactatgct tcaggctacc attatggagt ctggtcctgt    840

gagggctgca aggccttctt caagagaagt attcaaggac ataacgacta tatgtgtcca    900

gccaccaacc agtgcaccat tgataaaaac aggaggaaga gctgccaggc ctgccggctc    960

cgcaaatgct acgaagtggg aatgatgaaa ggtgggatac gaaaagaccg aagaggaggg   1020

agaatgttga aacacaagcg ccagagagat gatggggagg gcaggggtga agtggggtct   1080

gctggagaca tgagagctgc caacctttgg ccaagcccgc tcatgatcaa acgctctaag   1140

aagaacagcc tggccttgtc cctgacggcc gaccagatgg tcagtgcctt gttggatgct   1200

gagcccccca tactctattc cgagtatgat cctaccagac ccttcagtga agcttcgatg   1260

atgggcttac tgaccaacct ggcagacagg gagctggttc acatgatcaa ctgggcgaag   1320
```

```
agggtgccag gctttgtgga tttgaccctc catgatcagg tccaccttct agaatgtgcc   1380

tggctagaga tcctgatgat tggtctcgtc tggcgctcca tggagcaccc agggaagcta   1440

ctgtttgctc ctaacttgct cttggacagg aaccagggaa aatgtgtaga gggcatggtg   1500

gagatcttcg acatgctgct ggctacatca tctcggttcc gcatgatgaa tctgcaggga   1560

gaggagtttg tgtgcctcaa atctattatt ttgcttaatt ctggagtgta cacatttctg   1620

tccagcaccc tgaagtctct ggaagagaag gaccatatcc accgagtcct ggacaagatc   1680

acagacactt tgatccacct gatggccaag gcaggcctga ccctgcagca gcagcaccag   1740

cggctggccc agctcctcct catcctctcc cacatcaggc acatgagtaa caaaggcatg   1800

gagcatctgt acagcatgaa gtgcaagaac gtggtgcccc tctatgacct gctgctggag   1860

atgctggacg cccaccgcct acatgcgccc actagccgtg gaggggcatc cgtggaggag   1920

acggaccaaa gccacttggc cactgcgggc tctacttcat cgcattcctt gcaaaagtat   1980

tacatcacgg gggaggcaga gggtttccct gccacggtct gagagctccc tggctcccac   2040

acggttcaga taatccctgc tgcattttac cctcatcatg caccacttta gccaaattct   2100

gtctcctgca tacactccgg catgcatcca acaccaatgg ctttctagat gagtggccat   2160

tcatttgctt gctcagttct tagtggcaca tcttctgtct tctgttggga acagccaaag   2220

ggattccaag gctaaatctt tgtaacagct ctctttcccc cttgctatgt tactaagcgt   2280

gaggattccc gtagctcttc acagctgaac tcagtctatg ggttggggct cagataactc   2340

tgtgcattta agctacttgt agagacccag gcctggagag tagacatttt gcctctgata   2400

agcacttttt aaatggctct aagaataagc cacagcaaag aatttaaagt ggctccttta   2460

attggtgact tggagaaagc taggtcaagg gtttattata gcaccctctt gtattcctat   2520

ggcaatgcat ccttttatga aagtggtaca ccttaaagct tttatatgac tgtagcagag   2580

tatctggtga ttgtcaattc attcccccta taggaataca aggggcacac agggaaggca   2640

gatcccctag ttggcaagac tattttaact tgatacactg cagattcaga tgtgctgaaa   2700

gctctgcctc tggctttccg gtcatgggtt ccagttaatt catgcctccc atggacctat   2760

ggagagcagc aagttgatct tagttaagtc tccctatatg agggataagt tcctgatttt   2820

tgtttttatt tttgtgttac aaaagaaagc cctccctccc tgaacttgca gtaaggtcag   2880

cttcaggacc tgttccagtg ggcactgtac ttggatcttc ccggcgtgtg tgtgccttac   2940

acaggggtga actgttcact gtggtgatgc atgatgaggg taaatggtag ttgaaaggag   3000

caggggccct ggtgttgcat ttagccctgg ggcatggagc tgaacagtac ttgtgcagga   3060

ttgttgtggc tactagagaa caagagggaa agtagggcag aaactggata cagttctgag   3120

gcacagccag acttgctcag ggtggccctg ccacaggctg cagctaccta ggaacattcc   3180

ttgcagaccc cgcattgccc tttgggggtg ccctgggatc cctggggtag tccagctctt   3240

cttcatttcc cagcgtggcc ctggttggaa gaagcagctg tcacagctgc tgtagacagc   3300

tgtgttccta caattggccc agcaccctgg ggcacgggag aagggtgggg accgttgctg   3360

tcactactca ggctgactgg ggcctggtca gattacgtat gcccttggtg gtttagagat   3420

aatccaaaat cagggtttgg tttggggaag aaaatcctcc cccttcctcc cccgccccgt   3480

tccctaccgc ctccactcct gccagctcat ttccttcaat ttcctttgac ctataggcta   3540

aaaaagaaag gctcattcca gccacagggc agccttccct gggcctttgc ttctctagca   3600

caattatggg ttacttcctt tttcttaaca aaaaagaatg tttgatttcc tctgggtgac   3660
```

-continued

```
cttattgtct gtaattgaaa ccctattgag aggtgatgtc tgtgttagcc aatgacccag   3720
gtgagctgct cgggcttctc ttggtatgtc ttgtttggaa aagtggattt cattcatttc   3780
tgattgtcca gttaagtgat caccaaagga ctgagaatct gggagggcaa aaaaaaaaaa   3840
aaagttttta tgtgcactta aatttgggga caattttatg tatctgtgtt aaggatatgt   3900
ttaagaacat aattcttttg ttgctgtttg tttaagaagc accttagttt gtttaagaag   3960
caccttatat agtataatat atattttttt gaaattacat tgcttgttta tcagacaatt   4020
gaatgtagta attctgttct ggatttaatt tgactgggtt aacatgcaaa aaccaaggaa   4080
aaatatttag tttttttttt ttttttgta tacttttcaa gctaccttgt catgtataca   4140
gtcatttatg cctaaagcct ggtgattatt catttaaatg aagatcacat ttcatatcaa   4200
cttttgtatc cacagtagac aaaatagcac taatccagat gcctattgtt ggatactgaa   4260
tgacagacaa tcttatgtag caaagattat gcctgaaaag gaaaattatt cagggcagct   4320
aattttgctt ttaccaaaat atcagtagta atatttttgg acagtagcta atgggtcagt   4380
gggttctttt taatgtttat acttagattt tcttttaaaa aaattaaaat aaaacaaaaa   4440
aaaatttcta ggactagacg atgtaatacc agctaaagcc aaacaattat acagtggaag   4500
gttttacatt attcatccaa tgtgtttcta ttcatgttaa gatactacta catttgaagt   4560
gggcagagaa catcagatga ttgaaatgtt cgcccagggg tctccagcaa ctttggaaat   4620
ctctttgtat ttttacttga agtgccacta atggacagca gatattttct ggctgatgtt   4680
ggtattgggt gtaggaacat gatttaaaaa aaaactcttg cctctgcttt cccccactct   4740
gaggcaagtt aaaatgtaaa agatgtgatt tatctggggg gctcaggtat ggtggggaag   4800
tggattcagg aatctgggga atggcaaata tattaagaag agtattgaaa gtatttggag   4860
gaaaatggtt aattctgggt gtgcaccagg gttcagtaga gtccacttct gccctggaga   4920
ccacaaatca actagctcca tttacagcca tttctaaaat ggcagcttca gttctagaga   4980
agaaagaaca acatcagcag taaagtccat ggaatagcta gtggtctgtg tttcttttcg   5040
ccattgccta gcttgccgta atgattctat aatgccatca tgcagcaatt atgagaggct   5100
aggtcatcca aagagaagac cctatcaatg taggttgcaa aatctaaccc ctaaggaagt   5160
gcagtctttg atttgatttc cctagtaacc ttgcagatat gtttaaccaa gccatagccc   5220
atgccttttg agggctgaac aaataaggga cttactgata atttactttt gatcacatta   5280
aggtgttctc accttgaaat cttatacact gaaatggcca ttgatttagg ccactggctt   5340
agagtactcc ttcccctgca tgacactgat tacaaatact ttcctattca tactttccaa   5400
ttatgagatg gactgtgggt actgggagtg atcactaaca ccatagtaat gtctaatatt   5460
ctcaaaaggc aaccataatt ctctttggtg caggtcttgg gagcgtgatc tagattacac   5520
tgcaccattc ccaagttaat cccctgaaaa cttactctca actggagcaa atgaactttg   5580
gtcccaaata tccatctttt cagtagcgtt aattatgctc tgtttccaac tgcatttcct   5640
ttccaattga attaaagtgt ggcctcgttt ttagtcattt aaaattgttt tctaagtaat   5700
tgctgcctct attatggcac ttcaattttg cactgtcttt tgagattcaa gaaaaatttc   5760
tattcttttt tttgcatcca attgtgcctg aacttttaaa atatgtaaat gctgccatgt   5820
tccaaaccca tcgtcagtgt gtgtgtttag agctgtgcac cctagaaaca acatattgtc   5880
ccatgagcag gtgcctgaga cacagacccc tttgcattca cagagaggtc attggttata   5940
gagacttgaa ttaataagtg acattatgcc agtttctgtt ctctcacagg tgataaacaa   6000
tgctttttgt gcactacata ctcttcagtg tagagctctt gttttatggg aaaaggctca   6060
```

aatgccaaat tgtgtttgat ggattaatat gcccttttgc cgatgcatac tattactgat 6120
gtgactcggt tttgtcgcag ctttgctttg tttaatgaaa cacacttgta aacctctttt 6180
gcactttgaa aaagaatcca gcgggatgct cgagcacctg taaacaattt tctcaaccta 6240
tttgatgttc aaataaagaa ttaaactaaa 6270

<210> SEQ ID NO 5
<211> LENGTH: 1173
<212> TYPE: DNA
<213> ORGANISM: Homo sapiens

<400> SEQUENCE: 5
atgccgccct ccgggctgcg gctgctgctg ctgctgctac cgctgctgtg gctactggtg 60
ctgacgcctg gccggccggc cgcgggacta tccacctgca agactatcga catggagctg 120
gtgaagcgga agcgcatcga ggccatccgc ggccagatcc tgtccaagct gcggctcgcc 180 agcccccga gccaggggga ggtgccgccc ggcccgctgc ccgaggccgt gctcgccctg 240
tacaacagca cccgcgaccg ggtggccggg gagagtgcag aaccggagcc cgagcctgag 300
gccgactact acgccaagga ggtcacccgc gtgctaatgg tggaaaccca caacgaaatc 360
tatgacaagt tcaagcagag tacacacagc atatatatgt tcttcaacac atcagagctc 420
cgagaagcgg tacctgaacc cgtgttgctc tcccgggcag agctgcgtct gctgaggctc 480
aagttaaaag tggagcagca cgtggagctg taccagaaat acagcaacaa ttcctggcga 540
tacctcagca accggctgct ggcacccagc gactcgccag agtggttatc ttttgatgtc 600
accggagttg tgcggcagtg gttgagccgt ggaggggaaa ttgagggctt tcgccttagc 660
gcccactgct cctgtgacag cagggataac acactgcaag tggacatcaa cgggttcact 720
accggccgcc gaggtgacct ggccaccatt catggcatga accggccttt cctgcttctc 780
atggccaccc cgctggagag ggcccagcat ctgcaaagct cccggcaccg ccgagccctg 840
gacaccaact attgcttcag ctccacggag aagaactgct gcgtgcggca gctgtacatt 900
gacttccgca aggacctcgg ctggaagtgg atccacgagc ccaagggcta ccatgccaac 960
ttctgcctcg ggccctgccc ctacatttgg agcctggaca cgcagtacag caaggtcctg 1020
gccctgtaca accagcataa cccgggcgcc tcggcggcgc cgtgctgcgt gccgcaggcg 1080
ctggagccgc tgcccatcgt gtactacgtg ggccgcaagc ccaaggtgga gcagctgtcc 1140
aacatgatcg tgcgctcctg caagtgcagc tag 1173

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
ggaaaagaag gaagaagaat t 21

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
ggaaagccag aggaaccaat t 21

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
uucuccgaac gugucacgut t 21

<210> SEQ ID NO 9
<211> LENGTH: 23
<212> TYPE: DNA
<213> ORGANISM: Artificial Sequence
<220> FEATURE:
<223> OTHER INFORMATION: Synthetic

<400> SEQUENCE: 9
ggccagaacc uuccuccucu utt 23

<210> SEQ ID NO 10
<211> LENGTH: 22
<212> TYPE: DNA
<213> ORGANISM: Artificial Sequence
<220> FEATURE:
<223> OTHER INFORMATION: Synthetic

<400> SEQUENCE: 10
aaaagcuggg uugagagggc ga 22

<210> SEQ ID NO 11
<211> LENGTH: 21
<212> TYPE: DNA
<213> ORGANISM: Artificial Sequence
<220> FEATURE:
<223> OTHER INFORMATION: Synthetic

<400> SEQUENCE: 11
gccugagagu ggagguaact t 21

<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12
gcagcaagcg acagagaaat t 21

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
caaugacuga agaauucaat t 21

<210> SEQ ID NO 14
<211> LENGTH: 21
<212> TYPE: DNA
<213> ORGANISM: Artificial Sequence
<220> FEATURE:
<223> OTHER INFORMATION: Synthetic

<400> SEQUENCE: 14
guuccauugc uuggcgaaut t 21

<210> SEQ ID NO 15
<211> LENGTH: 23
<212> TYPE: DNA
<213> ORGANISM: Artificial Sequence
<220> FEATURE:
<223> OTHER INFORMATION: Synthetic

<400> SEQUENCE: 15
ugagguuggu guacugugug uga 23

<210> SEQ ID NO 16
<211> LENGTH: 21
<212> TYPE: DNA
<213> ORGANISM: Artificial Sequence
<220> FEATURE:
<223> OTHER INFORMATION: Synthetic

<400> SEQUENCE: 16
cggcugaccc augaaauaat t 21

<210> SEQ ID NO 17
<211> LENGTH: 21
<212> TYPE: DNA
<213> ORGANISM: Artificial Sequence
<220> FEATURE:
<223> OTHER INFORMATION: Synthetic

<400> SEQUENCE: 17
cacuguggac agcaaauaat t 21

<210> SEQ ID NO 18
<211> LENGTH: 21
<212> TYPE: DNA
<213> ORGANISM: Artificial Sequence
<220> FEATURE:
<223> OTHER INFORMATION: Synthetic

<400> SEQUENCE: 18
uauuaauuga agcaccacct t 21

<210> SEQ ID NO 19
<211> LENGTH: 21
<212> TYPE: DNA
<213> ORGANISM: Artificial Sequence
<220> FEATURE:
<223> OTHER INFORMATION: Synthetic

<400> SEQUENCE: 19
gcguaaucuc caggauaact t 21

<210> SEQ ID NO 20
<211> LENGTH: 23
<212> TYPE: DNA
<213> ORGANISM: Artificial Sequence
<220> FEATURE:
<223> OTHER INFORMATION: Synthetic

<400> SEQUENCE: 20
uuauugcuua agaauacgcg uag 23

```
<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21

cguuaauacu cacuguauat t                                              21


<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22

agaguccuuc gauagggact t                                              21


<210> SEQ ID NO 23
<211> LENGTH: 21
<212> TYPE: DNA
<213> ORGANISM: Artificial Sequence
<220> FEATURE:
<223> OTHER INFORMATION: Synthetic

<400> SEQUENCE: 23

uccccucucu aaggaaguct t                                              21


<210> SEQ ID NO 24
<211> LENGTH: 21
<212> TYPE: DNA
<213> ORGANISM: Artificial Sequence
<220> FEATURE:
<223> OTHER INFORMATION: Synthetic

<400> SEQUENCE: 24

gggacgaaga cgaacacuut t                                              21


<210> SEQ ID NO 25
<211> LENGTH: 21
<212> TYPE: DNA
<213> ORGANISM: Artificial Sequence
<220> FEATURE:
<223> OTHER INFORMATION: Synthetic

<400> SEQUENCE: 25

gacgaaguac cgaaagguct t                                              21


<210> SEQ ID NO 26
<211> LENGTH: 21
<212> TYPE: DNA
<213> ORGANISM: Artificial Sequence
<220> FEATURE:
<223> OTHER INFORMATION: Synthetic

<400> SEQUENCE: 26

aagaagggcg gaaagaucgt t                                              21


<210> SEQ ID NO 27
<211> LENGTH: 21
<212> TYPE: DNA
<213> ORGANISM: Artificial Sequence
<220> FEATURE:
<223> OTHER INFORMATION: Synthetic
```

<400> SEQUENCE: 27
guaaacaauc cggaagcgat t 21

<210> SEQ ID NO 28
<211> LENGTH: 21
<212> TYPE: DNA
<213> ORGANISM: Artificial Sequence
<220> FEATURE:
<223> OTHER INFORMATION: Synthetic

<400> SEQUENCE: 28
gagauuctcg caugccagat t 21

<210> SEQ ID NO 29
<211> LENGTH: 21
<212> TYPE: DNA
<213> ORGANISM: Artificial Sequence
<220> FEATURE:
<223> OTHER INFORMATION: Synthetic

<400> SEQUENCE: 29
gucgauguac acguucguct t 21

<210> SEQ ID NO 30
<211> LENGTH: 21
<212> TYPE: DNA
<213> ORGANISM: Artificial Sequence
<220> FEATURE:
<223> OTHER INFORMATION: Synthetic

<400> SEQUENCE: 30
cuggagagca accgcataat t 21

<210> SEQ ID NO 31
<211> LENGTH: 21
<212> TYPE: DNA
<213> ORGANISM: Artificial Sequence
<220> FEATURE:
<223> OTHER INFORMATION: Synthetic

<400> SEQUENCE: 31
gauucucgca ugccagagat t 21

<210> SEQ ID NO 32
<211> LENGTH: 21
<212> TYPE: DNA
<213> ORGANISM: Artificial Sequence
<220> FEATURE:
<223> OTHER INFORMATION: Synthetic

<400> SEQUENCE: 32
cauaaaggcc aagaagggct t 21

<210> SEQ ID NO 33
<211> LENGTH: 21
<212> TYPE: DNA
<213> ORGANISM: Artificial Sequence
<220> FEATURE:
<223> OTHER INFORMATION: Synthetic

<400> SEQUENCE: 33
caagaagggc ggaaagauct t 21

<210> SEQ ID NO 34

<211> LENGTH: 21
<212> TYPE: DNA
<213> ORGANISM: Artificial Sequence
<220> FEATURE:
<223> OTHER INFORMATION: Synthetic

<400> SEQUENCE: 34
auaaaggcca agaagggcgt t 21

<210> SEQ ID NO 35
<211> LENGTH: 21
<212> TYPE: DNA
<213> ORGANISM: Artificial Sequence
<220> FEATURE:
<223> OTHER INFORMATION: Synthetic

<400> SEQUENCE: 35
aucaggcaag gatatgggct t 21

<210> SEQ ID NO 36
<211> LENGTH: 21
<212> TYPE: DNA
<213> ORGANISM: Artificial Sequence
<220> FEATURE:
<223> OTHER INFORMATION: Synthetic

<400> SEQUENCE: 36
gaagagauac gcccugguut t 21

<210> SEQ ID NO 37
<211> LENGTH: 21
<212> TYPE: DNA
<213> ORGANISM: Artificial Sequence
<220> FEATURE:
<223> OTHER INFORMATION: Synthetic

<400> SEQUENCE: 37
uucgaaaugu ccguucggut t 21

<210> SEQ ID NO 38
<211> LENGTH: 21
<212> TYPE: DNA
<213> ORGANISM: Artificial Sequence
<220> FEATURE:
<223> OTHER INFORMATION: Synthetic

<400> SEQUENCE: 38
uuucugagga gccuucaggt t 21

<210> SEQ ID NO 39
<211> LENGTH: 21
<212> TYPE: DNA
<213> ORGANISM: Artificial Sequence
<220> FEATURE:
<223> OTHER INFORMATION: Synthetic

<400> SEQUENCE: 39
ucuaaggaag ucggggaagt t 21

<210> SEQ ID NO 40
<211> LENGTH: 47
<212> TYPE: RNA
<213> ORGANISM: Artificial Sequence
<220> FEATURE:
<223> OTHER INFORMATION: Synthetic

<400> SEQUENCE: 40
ggaacagaag gaagaagaag gccagaacca ggaaccuucc uccucuu 47

<210> SEQ ID NO 41
<211> LENGTH: 49
<212> TYPE: RNA
<213> ORGANISM: Artificial Sequence
<220> FEATURE:
<223> OTHER INFORMATION: Synthetic

<400> SEQUENCE: 41
ggaacgccag aagaagggcg gaaagaucga ggaaccaaag cuggguucc 49

<210> SEQ ID NO 42
<211> LENGTH: 40
<212> TYPE: RNA
<213> ORGANISM: Artificial Sequence
<220> FEATURE:
<223> OTHER INFORMATION: Synthetic

<400> SEQUENCE: 42
uucuccgaac gugucacgug gccagaaccu uccuccucuu 40

<210> SEQ ID NO 43
<211> LENGTH: 48
<212> TYPE: RNA
<213> ORGANISM: Artificial Sequence
<220> FEATURE:
<223> OTHER INFORMATION: Synthetic

<400> SEQUENCE: 43
acaagcuggg uuggggacga agacgaacac uuagagcccc ucuggcga 48

<210> SEQ ID NO 44
<211> LENGTH: 37
<212> TYPE: RNA
<213> ORGANISM: Artificial Sequence
<220> FEATURE:
<223> OTHER INFORMATION: Synthetic

<400> SEQUENCE: 44
gacgaaguac cgaaaaucga gagccggaag cgagguc 37

<210> SEQ ID NO 45
<211> LENGTH: 32
<212> TYPE: RNA
<213> ORGANISM: Artificial Sequence
<220> FEATURE:
<223> OTHER INFORMATION: Synthetic

<400> SEQUENCE: 45
gaagagauaa agggcgcgau ucucgccugg uu 32

<210> SEQ ID NO 46
<211> LENGTH: 33
<212> TYPE: RNA
<213> ORGANISM: Artificial Sequence
<220> FEATURE:
<223> OTHER INFORMATION: Synthetic

<400> SEQUENCE: 46
uucgaaaugu ccguaaggcc aagaaggguc ggu 33

<210> SEQ ID NO 47
<211> LENGTH: 26
<212> TYPE: RNA

<213> ORGANISM: Artificial Sequence
<220> FEATURE:
<223> OTHER INFORMATION: Synthetic

<400> SEQUENCE: 47
uuucugagga gccacguucg ucuuca 26

<210> SEQ ID NO 48
<211> LENGTH: 28
<212> TYPE: RNA
<213> ORGANISM: Artificial Sequence
<220> FEATURE:
<223> OTHER INFORMATION: Synthetic

<400> SEQUENCE: 48
gauucucgca ugcgcggaaa gacagaga 28

<210> SEQ ID NO 49
<211> LENGTH: 15
<212> TYPE: RNA
<213> ORGANISM: Artificial Sequence
<220> FEATURE:
<223> OTHER INFORMATION: Synthetic

<400> SEQUENCE: 49
aggccaagaa gggcg 15

<210> SEQ ID NO 50
<211> LENGTH: 16
<212> TYPE: RNA
<213> ORGANISM: Artificial Sequence
<220> FEATURE:
<223> OTHER INFORMATION: Synthetic

<400> SEQUENCE: 50
caagaagggc ggaaag 16

<210> SEQ ID NO 51
<211> LENGTH: 10
<212> TYPE: RNA
<213> ORGANISM: Artificial Sequence
<220> FEATURE:
<223> OTHER INFORMATION: Synthetic

<400> SEQUENCE: 51
agaguccuuc 10

<210> SEQ ID NO 52
<211> LENGTH: 12
<212> TYPE: RNA
<213> ORGANISM: Artificial Sequence
<220> FEATURE:
<223> OTHER INFORMATION: Synthetic

<400> SEQUENCE: 52
aacauccgga ag 12

<210> SEQ ID NO 53
<211> LENGTH: 8
<212> TYPE: RNA
<213> ORGANISM: Artificial Sequence
<220> FEATURE:
<223> OTHER INFORMATION: Synthetic

<400> SEQUENCE: 53 gcggaaag 8

```
<210> SEQ ID NO 54
<211> LENGTH: 9
<212> TYPE: RNA
<213> ORGANISM: Artificial Sequence
<220> FEATURE:
<223> OTHER INFORMATION: Synthetic

<400> SEQUENCE: 54

ucgacacgu                                                          9
```

DOUBLE-STRANDED RNA MOLECULES WITH STABILITY IN MAMMALIAN BODY FLUID, PREPARATION AND APPLICATION THEREOF

FIELD OF THE INVENTION

This invention relates to nucleic acid technology, specifically to the preparation and application of double-stranded RNA molecules that are stable in mammalian body fluids.

BACKGROUND OF THE INVENTION

RNA interference (RNAi), also known as post-transcriptional gene silencing (PTGS), is a phenomenon of shutting down homologous gene expression or gene silencing at mRNA level mediated by double-stranded RNA (dsRNA) molecules, RNAi was first reported in plants in 1990 by two different groups, and later on, this phenomenon was further observed in almost all eukaryotes, including *C. elegans, Drosophila*, zebrafish and mice (Napoli C, 1990; Fire A, 1991; Guo S, 1995). In 1999, RNA fragments of 21 to 25 nucleotides in length were identified in plant RNAi by Hamilton and Baulcombe. These small RNA fragments were demonstrated to be the mediator necessary for RNAi, and thus named as small interfering RNA (siRNA) (Hamilton A J, 1999). Double-stranded siRNA conjugates with endogenous enzymes and proteins, and then forms RNA-induced silencing complex (RISC). In the process of RNAi, while the sense RNA strand of double-stranded siRNA is released from the complex, the antisense RNA strand functions to guide RISC to target mRNA at homologous locus, resulting in the degradation of target mRNA and gene silencing mediated by RNase III component within the RISC complex (Zamore P D, 2000; Hammond S M, 2001).

In addition to gene function studies, siRNA was extensively used in treatment of human diseases, inhibiting diesease-causing gene expression in major diseases such as viral infection or tumor (Tiemann the K, 2009; Jackson, A L 2010). However, due to the low stability, siRNA is susceptive to degdation by ribonuclease which is abandent in blood (Czauderna F, 2003; Haupenthal J, 2006; Turner J J, 2007), thus synthetic siRNAs are often chemically modified to increase their stability in blood (Braasch D A, 2003; Layzer J M, 2004; Choung S2006). Even though chemical modification can fairly improve stability of siRNA in blood, however, the introduced modification results in increased potential cytotoxicity and compromised its biological activity in many cases. This therefore limits in vivo applications of the modified siRNAs.

Therefore, there is an urgent need to develop a strategy to enhance the stability of synthetic siRNAs in blood without increasing their in vivo toxicity, and hence to solve the technical bottleneck faced in the development of siRNA therapeutics.

REFERENCES

Braasch D A, Jensen S, Liu Y, Kaur K, Arar K, White M A and Corey D R (2003) RNA interference in mammalian cells by chemically-modified RNA. Biochemistry 42:7967

Choung S, Kim Y J, Kim S, Park H O and Choi Y C (2006) Chemical modification of siRNAs to improve serum stability without loss of efficacy. Biochem Biophys Res Commun. 342:919

Czauderna F, Fechtner M, Dames S, Aygün H, Klippel A, Pronk G J, Giese K and Kaufmann J (2003) Structural variations and stabilising modifications of synthetic siRNAs in mammalian cells. Nucleic Acids Res. 31:2705

Elbashir S M, Harborth J, Lendeckel W, Yalcin A, Weber K and Tuschl T (2001) Duplexes of 21-nucleotide RNAs mediate RNA interference in cultured mammalian cells. Nature 411:494

Fire A, Albertson D, Harrison S W and Moerman D G (1991) Production of antisense RNA leads to effective and specific inhibition of gene expression in *C. elegans* muscle. Development 113:503

Fire A, Xu S, Montgomery M K, Kostas S A, Driver S E and Mello C C (1998) Potent and specific genetic interference by double-stranded RNA in *Caenorhabditis elegans*. Nature 391:806

Guo S and Kemphues K J (1995) par-1, a gene required for establishing polarity in *C. elegans* embryos, encodes a putative Ser/Thr kinase that is asymmetrically distributed. Cell 81:611

Hamilton A J and Baulcombe D C (1999) A species of small antisense RNA in posttranscriptional gene silencing in plants. Science 286:950

Hammond S M, Boettcher S, Caudy A A, Kobayashi R and Hannon G J (2001) Argonaute2, a link between genetic and biochemical analyses of RNAi. Science 293:1146

Haupenthal J, Baehr C, Kiermayer S, Zeuzem S and Piiper A (2006) Inhibition of RNAse A family enzymes prevents degradation and loss of silencing activity of siRNAs in serum. Biochem Pharmacol. 71:702

Jackson A L and Linsley P S (2010) Recognizing and avoiding siRNA off-target effects for target identification and therapeutic application. Nat Rev Drug Discov. 9:57

Layzer J M, McCaffrey A P, Tanner A K, Huang Z, Kay M A and Sullenger B A (2004) In vivo activity of nuclease-resistant siRNAs. RNA 10:766

Napoli C, Lemieux C and Jorgensen R (1990) Introduction of a Chimeric Chalcone Synthase Gene into Petunia Results in Reversible Co-Suppression of Homologous Genes in trans. Plant Cell 2:279

Tiemann K and Rossi J J (2009) RNAi-based therapeutics-current status, challenges and prospects. EMBO Mol Med. 1:142

Turner J J, Jones S W, Moschos S A, Lindsay M A and Gait M J (2007) MALDI-TOF mass spectral analysis of siRNA degradation in serum confirms an RNAse A-like activity. Mol Biosyst 3:43

Zamore P D, Tuschl T, Sharp P A and Bartel D P (2000) RNAi: double-stranded RNA directs the ATP-dependent cleavage of mRNA at 21 to 23 nucleotide intervals. Cell 101(1):25

BRIEF DESCRIPTION OF THE DRAWINGS

FIG. 1 In vivo stability assay of siRNAs

1, Untreated siRNA; 2, Urine collected from siRNA-treated mice; 3, Urine collected from saline-treated mice.

DISCLOSURE OF THE INVENTION

The technical problem to be solved by the present invention is to provide double-stranded RNA molecules that are stable in mammalian body fluids.

To address the problem, in one aspect, the present invention provides an isolated double-stranded RNA molecule, characterized in that the double-stranded RNA molecule has at least one of the following sequence properties: 1) The content of UA/UA sequence is not greater than 10%; 2) The content of CA/UG and/or UG/CA sequence is not greater than 10%; 3)

The content of UA/UA and CA/UG and/or UG/CA sequence is not greater than 20%, and the content of UA/UA is not greater than 10%.

Preferably, the double-stranded RNA molecule is comprised of only unmodified nucleotides. The unmodified nucleotides are preferably naturally occurring nucleotides in mammals.

In the present invention, when the term "isolated" is used for RNA molecule, the RNA molecule is substantially free of other cellular components, preferably in a homogeneous state; the RNA can be in a solid form or in an aqueous solution. The purity and homogeneity of RNA are typically determined by chemical methods, such as polyacrylamide gel electrophoresis or high performance liquid chromatography.

In the present invention, the content of UA/UA and/or CA/UG and/or UG/CA of the RNA molecules refers to the percentage of UA/UA and/or CA/UG and/or UG/CA dinucleotide sequences in all the possible dinucleotide combinations within the RNA molecules.

The UA/UA dinucleotide sequence refers to the base-pairing of a continuous UA sequence on the first strand of the double-stranded RNA molecules and a continuous UA sequence on the second chain to form a complementary UA/UA dinucleotide sequence. The CA/UG dinucleotide sequence refers to the base-pairing of a continuous CA sequence on the first strand of the double-stranded RNA molecules and a continuous UG sequence on the second strand to form a complementary CA/UG sequence. The UG/CA dinucleotide sequence refers to the base-pairing of a continuous UG sequence on the first strand of the double-stranded RNA molecules and a continuous CA sequence on the second strand to form a complementary UG/CA sequence.

In the above embodiments, when the siRNA contains UA/UA sequence, the percentage of UA/UA sequence in all the possible dinucleotide combinations within the siRNA is not greater than 10%; preferably is not greater than 6%, more preferably is not greater than 3%, more preferably is not greater than 2%, and most preferably is equal to 0%; when the siRNA contains CA/UG sequence, the percentage of said CA/UG sequence in all the possible dinucleotide combinations within the siRNA is not greater than 20%, preferably is not greater than 17%, more preferably is not greater than 13%, more preferably is not greater than 12%, more preferably is not greater than 11%; more preferably is not greater than 10%, more preferably is not greater than 6%, more preferably is not greater than 3%, and most preferably is equal to 0%; when the siRNA contains UG/CA sequence, the percentage of UG/CA sequence in all the possible dinucleotide combinations within the siRNA is not greater than 20%, preferably is not greater than 17%, more preferably is not greater than 13%, more preferably is not greater than 12%, more preferably is not greater than 11%, more preferably is not greater than 10%, more preferably is not greater than 6%, more preferably is not greater than 3%, and most preferably is equal to 0%; when the double-stranded RNA contains both UA/UA and CA/UG sequences, or contains both UA/UA and UG/CA sequences, or contains UA/UA, CA/UG and UG/CA sequences, the total content of these sequences is not greater than 20%, preferably is not greater than 17%, more preferably is not greater than 12%, more preferably is not greater than 9%, more preferably is not greater than 8%, more preferably is not greater than 6%, and most preferably is equal to 0%, and the content of the UA/UA sequence is not greater than 10%, preferably is not greater than 6%, more preferably is not greater than 3%, more preferably is not greater than 2%, and most preferably is equal to 0%.

In the above embodiments, preferably the double-stranded RNA molecules do not contain UA/UA sequence; when the double-stranded RNA molecules contain CA/UG sequence, the percentage of the CA/UG sequence in all possible dinucleoside combinations is not greater than 10%, when the double-stranded RNA molecules contain UG/CA sequence, the percentage of the UG/CA sequence in all possible dinucleoside combinations is not greater than 10%.

Most preferably, the double-stranded RNA molecules do not contain any of the UA/UA, CA/UG or UG/CA sequences.

The double-stranded RNA molecules with the above-mentioned sequence properties remain stable in the mammalian body fluids, preferably remain stable in mammalian body fluids at 37° C. The mammals are selected from rats, mice, rabbits, dogs, sheep, pigs, cattles, monkeys and human. The mammalian body fluids are selected from blood, plasma, serum, tissue fluid, cerebrospinal fluid, saliva and secretions. Concentrations of the mammalian body fluids are of at least 10%, 20%, 50%, 90% or 100%. After contacting the double-stranded RNA molecules with the mammalian body fluids, at least 70%, 80%, 90%, or even 95% of the RNA molecule maintains intact double-stranded structure. The double-stranded RNA molecules with the above-mentioned sequence properties maintain stable in mammalian body fluids for a time longer than 10 minutes, preferably longer than 1 hour, more preferably longer than 6 hours, more preferably time longer than 12 hours.

Polyacrylamide gel was used to determine the stability of the siRNA in serum, and then quantitative software such as ImageJ was used to quantify the amount of each RNA bands. The integrity of the double-stranded RNA molecules was determined by dividing the amount of the treated samples by the amount of the initial samples. In the embodiments, siRNA stability is represented as the follows: "+" indicates that after treatment with serum, the main band of the siRNA disappeared completely, showing only visible degradation bands, the integrity of the RNA molecules is less than 70%; "++" indicates that after treatment with serum, the integrity of the double-stranded RNA molecules is more than 70%, while visible degradation bands were seen; "+++" indicates that after treatment with serum, the integrity of the double-stranded RNA molecules is more than 90%, and no obvious degradation bands were observed.

In the present invention, there is no particular restriction on the length of the double-stranded RNA molecules. For example, they can be long double-stranded RNAs with a length of tens to hundreds, or even thousands of nucleotides; they can also be short double-stranded RNAs, such as small interfering RNAs (siRNAs). In one preferred embodiment, the mammalian body fluid stable double-stranded RNA molecules are of a length of 8-50 nucleotides; preferably, the double-stranded RNA molecules are of a length of 10-40 nucleotides; more preferably, the double-stranded RNA molecules are of a length of 12-30 nucleotides. In another preferred embodiment of the present invention, the mammalian body fluid stable double-stranded RNA molecules are of 14-27 nucleotides in length, at least one of the component RNA strand contains a protruding 3' end of 1-5 nucleotides, the RNA molecules can exert gene-specific RNA interference.

In the second aspect of the present invention, it provides a method for preparing the double-stranded RNA molecules stable in mammalian body fluids, the method comprises the following steps:

(a) selecting one or more sequences of 18-30 nucleotides long from a target transcript sequence as a first strand of the double-stranded RNA molecule, wherein a second strand of the double-stranded RNA molecule is complementary to the first strand, wherein the double-stranded RNA molecule has at least one of the following sequence features: 1) the content of UA/UA sequence is not greater than 10%; 2) the content of CA/UG and/or UG/CA sequence is not greater than 10%; and 3) the content of UA/UA and CA/UG and/or UG/CA sequence is not greater than 20%, and the content of UA/UA is not greater than 10%;

(b) preparing the double-stranded RNA molecule; and (c) contacting the prepared double-stranded RNA molecule with solution containing at least 10% of mammalian body fluids for at least 10 minutes, wherein RNA molecule of which 70% maintain intact double-stranded structure is mammalian body fluid stabile double-stranded RNA molecule.

The present invention also provides a method for screening for double-stranded RNA molecule molecules stable in mammalian body fluids, comprising:

(a) selecting one or more sequences of 18-30 nucleotides long from a target transcript as the first strand of the double-stranded RNA molecule, wherein the second strand of the double-stranded RNA molecule is complementary to the first strand, wherein the double-stranded RNA molecule has at least one of the following sequence features: 1) the content of UA/UA sequence is not greater than 10%; 2) the content of CA/UG and/or UG/CA sequence is not greater than 10%; and 3) the content of UA/UA and CA/UG and/or UG/CA sequence is not greater than 20%, and the content of UA/UA is not greater than 10%;

(b) preparing the double-stranded RNA molecule; and (c) contacting the prepared double-stranded RNA molecule with a solution containing at least 10% of mammalian body fluids for at least 10 minutes, and selecting RNA molecule that maintain at least 70% intact double-stranded structure which a mammalian body fluid stabile double-stranded RNA molecule.

In a third aspect, the present invention provides the applications of the double-stranded RNA molecules.

First of all, the double-stranded RNA molecules can be used to inhibit gene expression in cells. Therefore, the present invention provides a method for inhibition of target gene expression in cells. The method comprises the following steps:

(a) introducing the double-stranded RNA molecules into at least one type of cells; and (b) culturing the cells until the target gene expression is inhibited.

Preferably, the cells are mammalian cells.

Secondly, the double-stranded RNA molecules of the present invention can also be used for preparing siRNA drugs or immunoadjuvants.

The present invention further provides a pharmaceutical composition for inhibiting the expression of a target gene in a mammal, wherein the pharmaceutical composition comprises at least one of the double-stranded RNA molecules provided herein and a pharmaceutically acceptable carrier. As used herein, "pharmaceutically acceptable carrier" should be compatible with the said double-stranded RNA molecules in the pharmaceutical compositions of the present invention. They can be mixed together without significantly compromising the gene inhibition effects of the pharmaceutical compositions. As specific examples of a pharmaceutically acceptable carrier or a component of, the pharmaceutically acceptable carrier includes sugars, such as lactose, glucose and sucrose; starch such as corn starch and potato starch; cellulose and its derivatives, such as carboxymethyl fiber sodium, ethyl cellulose and methyl cellulose; west tragacanth powder; malt; gelatin; talc; solid lubricant such as stearic acid and magnesium stearate; calcium sulfate; vegetable oil such as peanut oil, cottonseed oil, sesame oil, olive oil, corn oil and cocoa butter; polyols, such as propylene glycol, glycerol, sorbitol, mannose, alcohol and polyethylene glycol; alginate; emulsifiers, such as Tween; wetting agent, such as lauryl sulfate sodium; colorants; flavoring agent; pressure tablets, stabilizers; antioxidants; preservatives; pyrogen free water; isotonic salt solution; and phosphate buffer, preferably selected from the group consisting of saline, glycerol and phosphate buffer saline. The pharmaceutical compositions of this invention can be made in an acceptable variety of pharmaceutical formulations, can be administrated by physicians based on patient type, age, weight and approximate disease status, mode of administration and other factors to be beneficial to the patient. The formulations of the present invention include the oral solution, injection, sublingual agents to a variety of liquid formulations, or through appropriate excipient prepared into tablets, capsules, etc. a variety of other formulations. Preferably, the dosage forms of the pharmaceutical composition are selected from the injections, capsules, sublingual service, oral liquid, aerosol or patch.

In another preferred example of the present invention, it provides a method for preparing the pharmaceutical composition, wherein the method comprises formulating the double-stranded RNA molecules and a pharmaceutically acceptable carrier to obtain the pharmaceutical composition. There is no particular restriction on the order of formulating the double-stranded RNA molecules and the pharmaceutically acceptable carrier.

By choosing the nucleic acid sequence of the double-stranded RNA molecule to reduce the content of UA/UA and/or CA/UG and/or UG/CA dinucleotides, the present invention provides a method to increase its resistance to nuclease in mammalian body fluids, therefore to increase the stability of unmodified double-stranded RNA molecules in the mammalian body fluids. Compared to modified nucleic acid molecules, the present invention effectively reduces both cytotoxicity effects and compromising effects on its biological activity derived from the chemical modification used.

Given the disclosure of the present invention, the other aspects of the present invention are obvious to someone skilled in the art.

Since the phenomenon of RNA interference was discovered in 1998, siRNA therapeutics emerges gradually as an independent bio-pharmaceutical sector after years of development. As a revolutionary breakthrough in the field, the first siRNA drug Bevasiranib was approved for clinical trials in 2004 (Acuity Pharmaceuticals, for the treatment of wet age-related macular degeneration). The candidate drug entered into a Phase III clinical trial in 2008. The results of the clinical trials indicated that siRNA drugs were not only safe, but also featured by low toxicity and good efficacy. It is very promising to become a technology platform for large-scale drug development.

Nevertheless, there are many technological obstacles that have not been overcome in siRNA therapeutics, such as how to improve the stability of siRNA in blood and to prolong its duration in serum, how to improve its targeting effects, etc. In particular for systemic siRNA delivery, siRNA stabilizating technology is a prerequisite for optimizing serum duration and tissue targeting. Previous siRNA stabilizating technology was based on a variety of chemical modifications developed for antisense oligonucleotide and ribozyme, including 2-O-(2,4-dinitriophenyl) modification, 2'-fluoro-modified 2'-O-methyl modification. 2'-O-methoxyethyl modification, and LNA modification. Although these chemical modifications can significantly improve the stability of siRNAs, these modifications cause cytotoxicity effects, and therefore present new obstacles to the development of siRNA drugs.

Inventors of the present invention have carried out extensive and in-depth studies on how to enhance stability of siRNAs in serum, which led to the discovery of susceptibility sites for degradation of siRNA in serum. Based on this discovery, the inventors synthesized double-stranded RNA molecules without any chemical modification, and these double-stranded RNA molecules are stable in mammalian body fluids for long time.

The main advantages of the present invention are:

a) In prior art, mammalian body fluid-stable siRNAs are prepared by using chemical modifications or by non-natural nucleotide substitutions. The present invention, for the first time, provides a method to prepare mammalian body fluid-stable siRNA by using only unmodified natural nucleotides. The present invention improves siRNA resistance to nuclease degradation, and at the same time does not increase cytotoxicity of the RNA molecules.

b) The present invention provides a generally applicable technology for preparing mammalian body fluid-stable double-stranded RNA molecules targeting any specific gene.

The present invention is further illustrated in the following embodiments. It should be understood that these embodiments is only used to illustrate the invention rather than be used to limit the present invention. For the unspecified conditions in the implementations, conventional conditions specified in such as molecular cloning laboratory manual are used (Molecular cloning: A laboratory manual, 3rd ed., Sambrook, Cold Spring Biology—A Laboratory, Manual, Clark etc., Springer-Verlag, 1997), or in accordance with the conditions recommended by the manufacturer. Unless otherwise stated, reagents and media used in this invention are commercial products.

Example 1

Stability Assay of Double-Stranded RNA Molecules

4 μL 20 μM double-stranded RNA solution was added into a 36 μL 1×PBS solution containing a certain amount of fetal bovine serum, final serum concentrations are 10%, 20%, 50% or 90% respectively; the reaction system was incubated at 37° C. for 10 minutes, 30 minutes, 1 hour, or 6 hours before sampling; 10 μL sample was taken each time and immediately frozen in liquid nitrogen, and then stored at −80° C.

20% polyacrylamide ge was prepared by mixing each siRNA degradation sample of 10 μL with 3 μL of 3× loading buffer (30 mM EDTA, 36% glycerol, 0.06% bromine atmosphere blue) and was loaded onto the gel, electrophoresis was carried out under the condition of 80 mA constant current. After electrophoresis, the gel was stained with 1× Sybr Gold dye from Invitrogen (Cat. 11494) for 10 minutes and images were taken. Then, gray-scale quantitative software such as ImageJ was used to quantify the RNA bands. The integrity of the double-stranded RNA molecules was determined by dividing the amount of the treated samples by the amount of the initial samples.

siRNA stability is represented as follows: "+" indicates that after serum treatment, the main band of the siRNA completely disappeared, showing only visible degradation bands, the integrity of the RNA molecules is less than 70%; "++" indicates that after serum treatment, the integrity of the double-stranded RNA molecules is more than 70%, while visible degradation bands were seen; "+++" indicates that after serum treatment, the integrity of the double-stranded RNA molecules is more than 90%, and no obvious degradation bands were seen.

Example 2

Measurement of Gene Silencing Efficiency of siRNA

Human embryonic kidney cells (HEK293) were grown in a Dulbecco's modified Eagle's medium supplemented with 10% fetal bovine serum, 2 mM L-glutamine, 100 units/ml penicillin and 100 μg/ml streptomycin (Life Technologies, Gibco), and seeded into 24-well plates at a density of $1\times10^5$ cells (0.5 mL culture medium/well). After 24 hours incubation and the cell density reached 50% confluence, the culture medium was changed to Opti-MEM (Gibco). Lipofectamine™ 2000 transfection reagent (Invitrogen) was used to co-transfect siRNA and reporter plasmids. Reporting vector (0.17 μg/well) carrying the target site of tested siRNA and firefly luciferase gene were transfected into the cells together with pRL-TK control (0.017 μg/well) vector carrying renilla luciferase gene. The final concentration of siRNA was 13 nM. Each siRNA was parallelly transfected in three wells, with the same amount of the two reporter plasmids. The three wells without siRNA treatment were used as a control. Four hours after the transfection, the culture medium was changed to one milliliter of a DMEM growth medium (10% fetal bovine serum, 2 mM L-glutamine, 100 units/ml penicillin and 100 μg/ml streptomycin). Twenty-four later, the cells were harvested and lysated by adding 10 uL cell lysis buffer, and the activity of both luciferases was measured with a fluorometer (Synergy H T, BioTek, USA), using Dual-Luciferase reporter assay system (Promega) according to the manufacturer's instructions. Silencing efficacy of the siRNA was calculated by the following formula, using siRNA-untreated cells as a control. All the experiments were performed in triplicate and repeated for at least twice.

Inhibition ratio (%)=1−(Firefly luciferase expression levels of experimental group/Renilla luciferase expression levels of experimental group)/(Firefly luciferase expression levels of control group/Renilla luciferase expression levels of control group)×100%.

The present invention utilizes an isolated siRNA target site to measure the gene inhibition activity of siRNAs. Available literature and experimental data indicated that the inhibitory activity of a siRNA on an isolated target site is significantly correlated with its inhibition activity on an endogenous target gene (Huang H, Qiao R, Zhao D, Zhang T, Li Y, Yi F, Lai F, Hong J, Ding X, Yang Z, Zhang L, Du Q and Liang Z (2009). Profiling of mismatch discrimination in RNAi enabled rational design of allele-specific siRNAs. Nucleic Acids Res. 37(22):7560-9; Du Q, Thonberg H, Wang J, Wahlestedt C and Liang Z (2005) A systematic analysis of the silencing effects of an active siRNA at all single-nucleotide mismatched target sites. Nucleic Acids Res. 33(5):1671-7; Du Q, Thonberg H, Zhang H Y, Wahlestedt C and Liang Z (2004) Validating siRNA using a reporter made from synthetic DNA oligonucleotides. Biochem Biophys Res Commun. 325(1):243-9)

Example 3

Stability and Inhibition Activity of siRNA with Different UA/UA, CA/UG and/or UG/CA Content Based on the above study, the inventors of the present invention prepared siRNAs with varied contents of UA/UA, CA/UG and/or UG/CA. Using a protocol described in Example 1, we carried out stability assay of the siRNAs in serum. In details, we incubated the siRNA in a 10% serum solution for six hours at 37° C. before sampling. The gene inhibition activity of the siRNA was measured by using isolated siRNA target site. The experimental results are shown in Table 1. The experimental results showed that the stability of the siRNAs in serum are highly correlated with their UA/UA, CA/UG and/or UG/CA content, while there is no correlation between the gene silencing activity and siRNA stability.

TABLE 1

Serum stability of siRNAs

| Code | siRNA sequence | UA | CA | Stability | Inhibition |
|---|---|---|---|---|---|
| SEQ ID NO: 6 | 5'-GGAAAAGAAGGAAGAAGAATT-3' | 0% | 0% | +++ | 94% |
| SEQ ID NO: 7 | 5'-GGAAAGCCAGAGGAACCAATT-3' | 0% | 11% | +++ | 90% |
| SEQ ID NO: 8 | 5'-UUCUCCGAACGUGUCACGUTT-3' | 0% | 11% | +++ | 87% |
| SEQ ID NO: 9 | 5'-GGCCAGAACCUUCCUCCUCUUTT-3' | 0% | 6% | +++ | 83% |
| SEQ ID NO: 10 | 5'-AAAAGCUGGGUUGAGAGGGCGA-3' | 0% | 11% | +++ | 93% |
| SEQ ID NO: 11 | 5'-GCCUGAGAGUGGAGGUAACTT-3' | 6% | 11% | +++ | 98% |
| SEQ ID NO: 12 | 5'-GCAGCAAGCGACAGAGAAATT-3' | 0% | 17% | +++ | 95% |
| SEQ ID NO: 13 | 5'-CAAUGACUGAAGAAUUCAATT-3' | 0% | 22% | + | 97% |
| SEQ ID NO: 14 | 5'-GUUCCAUUGCUUGGCGAAUTT-3' | 0% | 17% | +++ | 75% |
| SEQ ID NO: 15 | 5'-UGAGGUUGGUGUACUGUGUGUGA-3' | 0% | 39% | + | 89% |
| SEQ ID NO: 16 | 5'-CGGCUGACCCAUGAAAUAATT-3' | 6% | 17% | + | 94% |
| SEQ ID NO: 17 | 5'-CACUGUGGACAGCAAAUAATT-3' | 6% | 28% | + | 95% |
| SEQ ID NO: 18 | 5'-UAUUAAUUGAAGCACCACCTT-3' | 11% | 17% | + | 99% |
| SEQ ID NO: 19 | 5'-GCGUAAUCUCCAGGAUAACTT-3' | 11% | 6% | + | 89% |
| SEQ ID NO: 20 | 5'-UUAUUGCUUAAGAAUACGCGUAG-3' | 22% | 6% | + | 79% |
| SEQ ID NO: 21 | 5'-CGUUAAUACUCACUGUAUATT-3' | 22% | 11% | + | 84% |

Example 4

Preparation and Investigation of Gene-Specific and Serum-Stabile siRNAs

In order to prepare serum-stabile siRNA targeting any specific gene or gene sequence fragment, the present invention established a technical protocol in accordance with Example 3, which comprises of the following steps: (a) selecting one or more sequences of 18-30 nucleotides long from a target transcript as the first strand of the double-stranded RNA molecule, wherein the second strand of the double-stranded RNA molecule is complementary to the first component strand, wherein the double-stranded RNA molecule has at least one of the following sequence features: 1) the content of UA/UA sequence is not greater than 10%; 2) the content of CA/UG and/or UG/CA sequence is not greater than 10%; and 3) the content of UA/UA and CA/UG and/or UG/CA sequence is not greater than 20%, and the content of UA/UA is not greater than 10%; (b) preparing the double-stranded RNA molecules; (c) contacting the prepared double-stranded RNA molecules with a solution containing a certain concentration of mammalian body fluids, obtain the RNA molecules that are stable in mammalian body fluid, (d) co-transfecting a reporter plasmid containing isolated siRNA target sites and the corresponding siRNA into cultured cells according to the protocol described in Example 2, and e) determining the expression levels of the reporter gene, therefore to obtain double-stranded siRNA molecules that are able to specifically inhibit the expression of the isolated target sites.

In accordance to the protocol described in Example 1, the siRNA was incubated with 10% serum under the condition of 37° C., RNA samples were taken six hours later and subjected to stability assay. The inhibitory activities on respective target sites were determined in accordance to the protocol described in Example 2 (results shown in Table 2).

TABLE 2

| Design and validation of serum stable siRNA | | | | | | |
|---|---|---|---|---|---|---|
| Code | Gene | siRNA sequence | UA | CA | Stability | Inhibition |
| SEQ ID NO: 22 | CVU47298 | 5'-AGAGUCCUUCGAUAGGGACtt-3' | 6% | 0% | +++ | 95% |
| SEQ ID NO: 23 | CVU47298 | 5'-UCCCCUCUCUAAGGAAGUCtt-3' | 6% | 0% | +++ | 92% |
| SEQ ID NO: 24 | CVU47298 | 5'-GGGACGAAGACGAACACUUtt-3' | 0% | 6% | +++ | 87% |
| SEQ ID NO: 25 | CVU47298 | 5'-GACGAAGUACCGAAAGGUCtt-3' | 6% | 0% | +++ | 93% |
| SEQ ID NO: 26 | CVU47298 | 5'-AAGAAGGGCGGAAAGAUCGtt-3' | 0% | 0% | +++ | 75% |
| SEQ ID NO: 27 | NM_000546 | 5'-GUAAACAAUCCGGAAGCGAtt-3' | 6% | 6% | +++ | 97% |
| SEQ ID NO: 28 | NM_000546 | 5'-GAGAUUCTCGCAUGCCAGAtt-3' | 0% | 17% | +++ | 88% |
| SEQ ID NO: 29 | NM_000546 | 5'-GUCGAUGUACACGUUCGUCtt-3' | 6% | 11% | +++ | 90% |
| SEQ ID NO: 30 | NM_007294.3 | 5'-CUGGAGAGCAACCGCAUAAtt-3' | 0% | 17% | +++ | 94% |
| SEQ ID NO: 31 | NM_007294.3 | 5'-GAUUCUCGCAUGCCAGAGAtt-3' | 0% | 17% | +++ | 97% |
| SEQ ID NO: 32 | NM_007294.3 | 5'-CAUAAAGGCCAAGAAGGGCtt-3' | 6% | 11% | +++ | 72% |
| SEQ ID NO: 33 | NM_007294.3 | 5'-CAAGAAGGGCGGAAAGAUCtt-3' | 0% | 6% | +++ | 94% |
| SEQ ID NO: 34 | NM_007294.3 | 5'-AUAAAGGCCAAGAAGGGCGtt-3' | 6% | 6% | +++ | 99% |
| SEQ ID NO: 35 | NM_000125 | 5'-AUCAGGCAAGGAUAUGGGCtt-3' | 0% | 11% | +++ | 87% |
| SEQ ID NO: 36 | NM_000125 | 5'-GAAGAGAUACGCCCUGGUUtt-3' | 6% | 6% | +++ | 89% |
| SEQ ID NO: 37 | NM_000125 | 5'-UUCGAAAUGUCCGUUCGGUtt-3' | 0% | 6% | +++ | 98% |
| SEQ ID NO: 38 | BT007245.1 | 5'-UUUCUGAGGAGCCUUCAGGtt-3' | 0% | 11% | +++ | 94% |
| SEQ ID NO: 39 | BT007245.1 | 5'-UCUAAGGAAGUCGGGGAAGtt-3' | 6% | 0% | +++ | 97% |

Example 5

Stability Assay of Long Double-Stranded RNAs in Serum

In addition to be used in the form of siRNA for regulating the expression of homologous target genes, double-stranded RNAs are also widely used as immune adjuvants, regulating the immune system. To verify the immune adjuvant application of the stable double-stranded RNAs which were prepared in the present invention by using only unmodified nucleotides, the inventors prepared long double-stranded RNA molecules with lengths between 8-50 bp. In accordance to the protocol described in Example 1, stability of the RNAs in serum was investigated by incubating the RNAs with 10% serum under the condition of 37° C., RNA samples were taken six hours later and subjected to stability assay. The experiment results are presented in Table 3.

TABLE 3

| Stability of siRNAs of different length in serum | | | | | |
|---|---|---|---|---|---|
| Code | Length | siRNA sequence | UA | CA | Stability |
| SEQ ID NO: 40 | 47 | 5'-GGAACAGAAGGAAGAAGAAGGCCAG AACCAGGAACCUUCCUCCUCUU-3' | 0% | 7% | +++ |
| SEQ ID NO: 41 | 49 | 5'-GGAACGCCAGAAGAAGGGCGGAAAG AUCGAGGAACCAAAGCUGGGUUCC-3' | 0% | 6% | +++ |
| SEQ ID NO: 42 | 40 | 5'-UUCUCCGAACGUGUCACGUGGCCAG AACCUUCCUCCUCUU-3' | 0% | 10% | +++ |
| SEQ ID NO: 43 | 48 | 5'-ACAAGCUGGGUUGGGGACGAAGACG AACACUUAGAGCCCCUCUGGCGA-3' | 2% | 6% | +++ |
| SEQ ID NO: 44 | 37 | 5'-GACGAAGUACCGAAAAUCGAGAGCC GGAAGCGAGGUC-3' | 3% | 0% | +++ |
| SEQ ID NO: 45 | 32 | 5'-GAAGAGAUAAAGGGCGCGAU UCUCGCCUGGUU-3' | 3% | 3% | +++ |
| SEQ ID NO: 46 | 33 | 5'-UUCGAAAUGUCCGUAAGGCC AAGAAGGGUCGGU-3' | 3% | 6% | +++ |

TABLE 3 -continued

| Stability of siRNAs of different length in serum | | | | | |
|---|---|---|---|---|---|
| Code | Length | siRNA sequence | UA | CA | Stability |
| SEQ ID NO: 47 | 26 | 5'-UUUCUGAGGAGCCACGUUCG UCUUCA-3 | 0% | 12% | +++ |
| SEQ ID NO: 48 | 28 | 5'-GAUUCUCGCAUGCGCGGAAAG ACAGAGA-3' | 0% | 11% | +++ |
| SEQ ID NO: 49 | 15 | 5'-AGGCCAAGAAGGGCG-3' | 0% | 7% | +++ |
| SEQ ID NO: 50 | 16 | 5'-CAAGAAGGGCGGAAAG-3' | 0% | 7% | +++ |
| SEQ ID NO: 51 | 10 | 5'-AGAGUCCUUC-3' | 0% | 0% | +++ |
| SEQ ID NO: 52 | 12 | 5'-AACAUCCGGAAG-3' | 0% | 9% | +++ |
| SEQ ID NO: 53 | 8 | 5'-GCGGAAAG-3' | 0% | 0% | +++ |
| SEQ ID NO: 54 | 9 | 5'-UCGACACGU-3' | 0% | 13% | +++ |

Example 6

Stability Assay of Serum-Stable siRNA in Mammalian Blood and Components

To further validate the stability of fetal bovine serum stable siRNAs provided in Example 3 and 4, we obtained whole blood from mice, rats, rabbits, cattle, rhesus monkey and human, and isolated the plasma and serum components. In accordance to the protocol described in Example 1, the stability of the siRNAs provided in Example 3 and 4 were further tested with these plasm and serum. In details, stability of the RNAs in serum was investigated by incubating the RNAs with 10% serum under the condition of 37° C., RNA samples were taken six hours later and subjected to stability assay. The experiment results are presented in Table 4.

Procedure for serum and plasma separation:

(a) Serum separation procedure: Whole blood was collected from animals, solidated naturally at room temperature, incubated at 37° C. for 1 hour and stored overnight in a 4° C. refrigerator. Serum was then separated from contracted blood clot.

(b) Plasma separation procedure: Plasma was separated from whole blood by using conventional centrifugation procedure to remove blood cells.

TABLE 4

| siRNA stability in blood, plasma and serum | | | | |
|---|---|---|---|---|
| Code | Species | Blood | Plasma | Serum |
| SEQ ID NO: 22 | mouse | +++ | +++ | +++ |
| SEQ ID NO: 23 | mouse | +++ | +++ | +++ |
| SEQ ID NO: 24 | mouse | +++ | +++ | +++ |
| SEQ ID NO: 25 | mouse | +++ | +++ | +++ |
| SEQ ID NO: 26 | mouse | +++ | +++ | +++ |
| SEQ ID NO: 27 | mouse | +++ | +++ | +++ |
| SEQ ID NO: 28 | mouse | +++ | +++ | +++ |
| SEQ ID NO: 29 | mouse | +++ | +++ | +++ |
| SEQ ID NO: 30 | mouse | +++ | +++ | +++ |
| SEQ ID NO: 31 | mouse | +++ | +++ | +++ |
| SEQ ID NO: 32 | mouse | +++ | +++ | +++ |
| SEQ ID NO: 33 | mouse | +++ | +++ | +++ |
| SEQ ID NO: 34 | mouse | +++ | +++ | +++ |
| SEQ ID NO: 35 | mouse | +++ | +++ | +++ |
| SEQ ID NO: 36 | mouse | +++ | +++ | +++ |
| SEQ ID NO: 37 | mouse | +++ | +++ | +++ |

TABLE 4-continued

| siRNA stability in blood, plasma and serum | | | | |
|---|---|---|---|---|
| Code | Species | Blood | Plasma | Serum |
| SEQ ID NO: 38 | mouse | +++ | +++ | +++ |
| SEQ ID NO: 39 | mouse | +++ | +++ | +++ |
| SEQ ID NO: 40 | mouse | +++ | +++ | +++ |
| SEQ ID NO: 41 | mouse | +++ | +++ | +++ |
| SEQ ID NO: 42 | mouse | +++ | +++ | +++ |
| SEQ ID NO: 43 | mouse | +++ | +++ | +++ |
| SEQ ID NO: 44 | mouse | +++ | +++ | +++ |
| SEQ ID NO: 45 | mouse | +++ | +++ | +++ |
| SEQ ID NO: 46 | mouse | +++ | +++ | +++ |
| SEQ ID NO: 47 | mouse | +++ | +++ | +++ |
| SEQ ID NO: 48 | mouse | +++ | +++ | +++ |
| SEQ ID NO: 49 | mouse | +++ | +++ | +++ |
| SEQ ID NO: 50 | mouse | +++ | +++ | +++ |
| SEQ ID NO: 51 | mouse | +++ | +++ | +++ |
| SEQ ID NO: 52 | mouse | +++ | +++ | +++ |
| SEQ ID NO: 53 | mouse | +++ | +++ | +++ |
| SEQ ID NO: 54 | mouse | +++ | +++ | +++ |
| SEQ ID NO: 22 | rat | +++ | +++ | +++ |
| SEQ ID NO: 23 | rat | +++ | +++ | +++ |
| SEQ ID NO: 24 | rat | +++ | +++ | +++ |
| SEQ ID NO: 25 | rat | +++ | +++ | +++ |
| SEQ ID NO: 26 | rat | +++ | +++ | +++ |
| SEQ ID NO: 27 | rat | +++ | +++ | +++ |
| SEQ ID NO: 28 | rat | +++ | +++ | +++ |
| SEQ ID NO: 29 | rat | +++ | +++ | +++ |
| SEQ ID NO: 30 | rat | +++ | +++ | +++ |
| SEQ ID NO: 31 | rat | +++ | +++ | +++ |
| SEQ ID NO: 32 | rat | +++ | +++ | +++ |
| SEQ ID NO: 33 | rat | +++ | +++ | +++ |
| SEQ ID NO: 34 | rat | +++ | +++ | +++ |
| SEQ ID NO: 35 | rat | +++ | +++ | +++ |
| SEQ ID NO: 36 | rat | +++ | +++ | +++ |
| SEQ ID NO: 37 | rat | +++ | +++ | +++ |
| SEQ ID NO: 38 | rat | +++ | +++ | +++ |
| SEQ ID NO: 39 | rat | +++ | +++ | +++ |
| SEQ ID NO: 40 | rat | +++ | +++ | +++ |
| SEQ ID NO: 41 | rat | +++ | +++ | +++ |
| SEQ ID NO: 42 | rat | +++ | +++ | +++ |
| SEQ ID NO: 43 | rat | +++ | +++ | +++ |
| SEQ ID NO: 44 | rat | +++ | +++ | +++ |
| SEQ ID NO: 45 | rat | +++ | +++ | +++ |
| SEQ ID NO: 46 | rat | +++ | +++ | +++ |
| SEQ ID NO: 47 | rat | +++ | +++ | +++ |
| SEQ ID NO: 48 | rat | +++ | +++ | +++ |
| SEQ ID NO: 49 | rat | +++ | +++ | +++ |
| SEQ ID NO: 50 | rat | +++ | +++ | +++ |
| SEQ ID NO: 51 | rat | +++ | +++ | +++ |
| SEQ ID NO: 52 | rat | +++ | +++ | +++ |

TABLE 4-continued siRNA stability in blood, plasma and serum

| Code | Species | Blood | Plasma | Serum |
|---|---|---|---|---|
| SEQ ID NO: 53 | rat | +++ | +++ | +++ |
| SEQ ID NO: 54 | rat | +++ | +++ | +++ |
| SEQ ID NO: 22 | Rabbit | +++ | +++ | +++ |
| SEQ ID NO: 23 | Rabbit | +++ | +++ | +++ |
| SEQ ID NO: 24 | Rabbit | +++ | +++ | +++ |
| SEQ ID NO: 25 | Rabbit | +++ | +++ | +++ |
| SEQ ID NO: 26 | Rabbit | +++ | +++ | +++ |
| SEQ ID NO: 27 | Rabbit | +++ | +++ | +++ |
| SEQ ID NO: 28 | Rabbit | +++ | +++ | +++ |
| SEQ ID NO: 29 | Rabbit | +++ | +++ | +++ |
| SEQ ID NO: 30 | Rabbit | +++ | +++ | +++ |
| SEQ ID NO: 31 | Rabbit | +++ | +++ | +++ |
| SEQ ID NO: 32 | Rabbit | +++ | +++ | +++ |
| SEQ ID NO: 33 | Rabbit | +++ | +++ | +++ |
| SEQ ID NO: 34 | Rabbit | +++ | +++ | +++ |
| SEQ ID NO: 35 | Rabbit | +++ | +++ | +++ |
| SEQ ID NO: 36 | Rabbit | +++ | +++ | +++ |
| SEQ ID NO: 37 | Rabbit | +++ | +++ | +++ |
| SEQ ID NO: 38 | Rabbit | +++ | +++ | +++ |
| SEQ ID NO: 39 | Rabbit | +++ | +++ | +++ |
| SEQ ID NO: 40 | Rabbit | +++ | +++ | +++ |
| SEQ ID NO: 41 | Rabbit | +++ | +++ | +++ |
| SEQ ID NO: 42 | Rabbit | +++ | +++ | +++ |
| SEQ ID NO: 43 | Rabbit | +++ | +++ | +++ |
| SEQ ID NO: 44 | Rabbit | +++ | +++ | +++ |
| SEQ ID NO: 45 | Rabbit | +++ | +++ | +++ |
| SEQ ID NO: 46 | Rabbit | +++ | +++ | +++ |
| SEQ ID NO: 47 | Rabbit | +++ | +++ | +++ |
| SEQ ID NO: 48 | Rabbit | +++ | +++ | +++ |
| SEQ ID NO: 49 | Rabbit | +++ | +++ | +++ |
| SEQ ID NO: 50 | Rabbit | +++ | +++ | +++ |
| SEQ ID NO: 51 | Rabbit | +++ | +++ | +++ |
| SEQ ID NO: 52 | Rabbit | +++ | +++ | +++ |
| SEQ ID NO: 53 | Rabbit | +++ | +++ | +++ |
| SEQ ID NO: 54 | Rabbit | +++ | +++ | +++ |
| SEQ ID NO: 22 | Bovine | +++ | +++ | +++ |
| SEQ ID NO: 23 | Bovine | +++ | +++ | +++ |
| SEQ ID NO: 24 | Bovine | +++ | +++ | +++ |
| SEQ ID NO: 25 | Bovine | +++ | +++ | +++ |
| SEQ ID NO: 26 | Bovine | +++ | +++ | +++ |
| SEQ ID NO: 27 | Bovine | +++ | +++ | +++ |
| SEQ ID NO: 28 | Bovine | +++ | +++ | +++ |
| SEQ ID NO: 29 | Bovine | +++ | +++ | +++ |
| SEQ ID NO: 30 | Bovine | +++ | +++ | +++ |
| SEQ ID NO: 31 | Bovine | +++ | +++ | +++ |
| SEQ ID NO: 32 | Bovine | +++ | +++ | +++ |
| SEQ ID NO: 33 | Bovine | +++ | +++ | +++ |
| SEQ ID NO: 34 | Bovine | +++ | +++ | +++ |
| SEQ ID NO: 35 | Bovine | +++ | +++ | +++ |
| SEQ ID NO: 36 | Bovine | +++ | +++ | +++ |
| SEQ ID NO: 37 | Bovine | +++ | +++ | +++ |
| SEQ ID NO: 38 | Bovine | +++ | +++ | +++ |
| SEQ ID NO: 39 | Bovine | +++ | +++ | +++ |
| SEQ ID NO: 40 | Bovine | +++ | +++ | +++ |
| SEQ ID NO: 41 | Bovine | +++ | +++ | +++ |
| SEQ ID NO: 42 | Bovine | +++ | +++ | +++ |
| SEQ ID NO: 43 | Bovine | +++ | +++ | +++ |
| SEQ ID NO: 44 | Bovine | +++ | +++ | +++ |
| SEQ ID NO: 45 | Bovine | +++ | +++ | +++ |
| SEQ ID NO: 46 | Bovine | +++ | +++ | +++ |
| SEQ ID NO: 47 | Bovine | +++ | +++ | +++ |
| SEQ ID NO: 48 | Bovine | +++ | +++ | +++ |
| SEQ ID NO: 49 | Bovine | +++ | +++ | +++ |
| SEQ ID NO: 50 | Bovine | +++ | +++ | +++ |
| SEQ ID NO: 51 | Bovine | +++ | +++ | +++ |
| SEQ ID NO: 52 | Bovine | +++ | +++ | +++ |
| SEQ ID NO: 53 | Bovine | +++ | +++ | +++ |
| SEQ ID NO: 54 | Bovine | +++ | +++ | +++ |
| SEQ ID NO: 22 | Rhesus | +++ | +++ | +++ |
| SEQ ID NO: 23 | Rhesus | +++ | +++ | +++ |
| SEQ ID NO: 24 | Rhesus | +++ | +++ | +++ |
| SEQ ID NO: 25 | Rhesus | +++ | +++ | +++ |
| SEQ ID NO: 26 | Rhesus | +++ | +++ | +++ |
| SEQ ID NO: 27 | Rhesus | +++ | +++ | +++ |
| SEQ ID NO: 28 | Rhesus | +++ | +++ | +++ |
| SEQ ID NO: 29 | Rhesus | +++ | +++ | +++ |

TABLE 4-continued siRNA stability in blood, plasma and serum

| Code | Species | Blood | Plasma | Serum |
|---|---|---|---|---|
| SEQ ID NO: 30 | Rhesus | +++ | +++ | +++ |
| SEQ ID NO: 31 | Rhesus | +++ | +++ | +++ |
| SEQ ID NO: 32 | Rhesus | +++ | +++ | +++ |
| SEQ ID NO: 33 | Rhesus | +++ | +++ | +++ |
| SEQ ID NO: 34 | Rhesus | +++ | +++ | +++ |
| SEQ ID NO: 35 | Rhesus | +++ | +++ | +++ |
| SEQ ID NO: 36 | Rhesus | +++ | +++ | +++ |
| SEQ ID NO: 37 | Rhesus | +++ | +++ | +++ |
| SEQ ID NO: 38 | Rhesus | +++ | +++ | +++ |
| SEQ ID NO: 39 | Rhesus | +++ | +++ | +++ |
| SEQ ID NO: 40 | Rhesus | +++ | +++ | +++ |
| SEQ ID NO: 41 | Rhesus | +++ | +++ | +++ |
| SEQ ID NO: 42 | Rhesus | +++ | +++ | +++ |
| SEQ ID NO: 43 | Rhesus | +++ | +++ | +++ |
| SEQ ID NO: 44 | Rhesus | +++ | +++ | +++ |
| SEQ ID NO: 45 | Rhesus | +++ | +++ | +++ |
| SEQ ID NO: 46 | Rhesus | +++ | +++ | +++ |
| SEQ ID NO: 47 | Rhesus | +++ | +++ | +++ |
| SEQ ID NO: 48 | Rhesus | +++ | +++ | +++ |
| SEQ ID NO: 49 | Rhesus | +++ | +++ | +++ |
| SEQ ID NO: 50 | Rhesus | +++ | +++ | +++ |
| SEQ ID NO: 51 | Rhesus | +++ | +++ | +++ |
| SEQ ID NO: 52 | Rhesus | +++ | +++ | +++ |
| SEQ ID NO: 53 | Rhesus | +++ | +++ | +++ |
| SEQ ID NO: 54 | Rhesus | +++ | +++ | +++ |
| SEQ ID NO: 22 | Human | +++ | +++ | +++ |
| SEQ ID NO: 23 | Human | +++ | +++ | +++ |
| SEQ ID NO: 24 | Human | +++ | +++ | +++ |
| SEQ ID NO: 25 | Human | +++ | +++ | +++ |
| SEQ ID NO: 26 | Human | +++ | +++ | +++ |
| SEQ ID NO: 27 | Human | +++ | +++ | +++ |
| SEQ ID NO: 28 | Human | +++ | +++ | +++ |
| SEQ ID NO: 29 | Human | +++ | +++ | +++ |
| SEQ ID NO: 30 | Human | +++ | +++ | +++ |
| SEQ ID NO: 31 | Human | +++ | +++ | +++ |
| SEQ ID NO: 32 | Human | +++ | +++ | +++ |
| SEQ ID NO: 33 | Human | +++ | +++ | +++ |
| SEQ ID NO: 34 | Human | +++ | +++ | +++ |
| SEQ ID NO: 35 | Human | +++ | +++ | +++ |
| SEQ ID NO: 36 | Human | +++ | +++ | +++ |
| SEQ ID NO: 37 | Human | +++ | +++ | +++ |
| SEQ ID NO: 38 | Human | +++ | +++ | +++ |
| SEQ ID NO: 39 | Human | +++ | +++ | +++ |
| SEQ ID NO: 40 | Human | +++ | +++ | +++ |
| SEQ ID NO: 41 | Human | +++ | +++ | +++ |
| SEQ ID NO: 42 | Human | +++ | +++ | +++ |
| SEQ ID NO: 43 | Human | +++ | +++ | +++ |
| SEQ ID NO: 44 | Human | +++ | +++ | +++ |
| SEQ ID NO: 45 | Human | +++ | +++ | +++ |
| SEQ ID NO: 46 | Human | +++ | +++ | +++ |
| SEQ ID NO: 47 | Human | +++ | +++ | +++ |
| SEQ ID NO: 48 | Human | +++ | +++ | +++ |
| SEQ ID NO: 49 | Human | +++ | +++ | +++ |
| SEQ ID NO: 50 | Human | +++ | +++ | +++ |
| SEQ ID NO: 51 | Human | +++ | +++ | +++ |
| SEQ ID NO: 52 | Human | +++ | +++ | +++ |
| SEQ ID NO: 53 | Human | +++ | +++ | +++ |
| SEQ ID NO: 54 | Human | +++ | +++ | +++ |

Example 6

In Vivo Stability Assay of Stable siRNAs

An important aspect of siRNA stabilization is the development of therapeutic siRNA. To further characterize the in vivo stability of these siRNAs, four stable siRNAs (SEQ ID NO: 6, SEQ ID NO:8, SEQ ID NO: 26 and SEQ ID NO: 27) were selected and injected in mice. The in vivo stability of the siRNAs was studied by examining the integrity of the siRNAs obtained from urine samples (FIG. 1).

(a) Mouse breeding and all the experimental procedures are approved by the Animal Ethics Committee of Peking University.

(b) Obtain male C57 mice of age 8-12 weeks and body weight about 18-22 grams at use. Using a dose of 2.5 mg/kg, 0.2 ml siRNA solution was intravenously injected into the mice. One hour after injection, mice were sacrificed and urine was directly collected from bladder. 10 ul of urine was examined by polyacrylamide gel electrophoresis.

(c) Prepare a 20% polyacrylamide gel, mix each siRNA sample with 3 μL of 3× loading buffer (30 mM EDTA, 36% glycerol, 0.06% bromine atmosphere blue) and then load onto the gel. Electrophoresis was performed under the condition of 80 mA constant current. After electrophoresis, stain the gel with 1× Sybr Gold dye from Invitrogen (Cat. 11494) for 10 minutes and take image.

FIG. 1 shows that siRNAs isolated from mouse urine are intact. This result indicates that siRNAs are stable in the in vivo metabolism procedure.

The invention claimed is:

1. An isolated, synthesized small interfering RNA molecule, wherein the RNA molecule has at least one of the following sequence properties:

the content of CA/UG and/or UG/CA sequence is not greater than 3%; and the content of the combination of UA/UA and (CA/UG and/or UG/CA) sequence is not greater than 10%.

2. The RNA molecule of claim 1, wherein the RNA molecule is comprised of only unmodified natural nucleotides.

3. The RNA molecule of claims 1 to 2, wherein the length of the double-stranded part is from 8 to 50 nucleotides.

4. The RNA molecule of claims 1 to 2, wherein the length of the double-stranded part is from 14 to 27 nucleotides, and at least one of the RNA strand contains a protruding 3' end of 1-5 nucleotides, wherein said RNA molecule can exert gene-specific RNA interference.

5. The RNA molecule of claim 1, wherein said RNA molecule is stable in mammalian body fluids of a mammalian animal for a time longer than 10 minutes; preferably, said RNA molecule is stable in mammalian body fluids for a time longer than 30 minutes; more preferably, said RNA molecule is stable in mammalian body fluids for a time longer than 1 hour; most preferably, said RNA molecule is stable in mammalian body fluids for a time longer than 6 hour.

6. The RNA molecule of claim 1, wherein 70% of said RNA molecule maintain integrity double-stranded structure after contacting with mammalian body fluids; preferably, 90% of said RNA molecule maintain integrity double-stranded structure after contacting with mammalian body fluids.

7. The RNA molecule of claim 5, wherein said mammalian animal is selected from the group consisting of rat, mouse, rabbit, dog, monkey, and human.

8. The RNA molecule of claim 5, wherein said mammalian body fluids are selected from the group consisting of blood, plasma, serum, tissue fluid, cerebrospinal fluid, saliva and secretions.

9. A method for preparing the RNA molecule of claim 1, comprising:

(a) selecting one or more sequences of 18-30 nucleotides long from a target transcript as the first strand of the RNA molecule, wherein the second strand of the RNA molecule is complementary to the first component strand, wherein the RNA molecule has at least one of the following sequence features: 1) the content of UA/UA sequence is not greater than 10%; 2) the content of CA/UG and/or UG/CA sequence is not greater than 10%; and 3) the content of UA/UA and CA/UG and/or UG/CA sequence is not greater than 20%, and the content of UA/UA is not greater than 10%;

(b) preparing said RNA molecule; and (c) contacting the prepared RNA molecule with a solution containing at least 10% of mammalian body fluids for at least 10 minutes, wherein RNA molecule that maintains at least 70% double-stranded structure integrity is mammalian body fluid stabile double-stranded RNA molecule.

10. A method for screening the RNA molecule of claim 1, comprising:

(a) selecting one or more sequences of 18-30 nucleotides long from a target transcript as the first strand of the RNA molecule, wherein the second strand of the RNA molecule is complementary to the first component strand, wherein the RNA molecule has at least one of the following sequence features: 1) the content of UA/UA sequence is not greater than 10%; 2) the content of CA/UG and/or UG/CA sequence is not greater than 10%; and 3) the content of UA/UA and CA/UG and/or UG/CA sequence is not greater than 20%, and the content of UA/UA is not greater than 10%;

(b) preparing said RNA molecule; and (c) contacting the prepared RNA molecule with a solution containing at least 10% of mammalian body fluids for at least 10 minutes, wherein RNA molecule that maintains at least 70% double-stranded structure integrity is mammalian body fluid stabile double-stranded RNA molecule.

11. A method for inhibiting the expression of a target gene in a cell, comprising:

(a) introducing the RNA molecule of claim 1 into the cell; and (b) incubating the cell for a time sufficient to inhibit the expression of the target gene in the cell.

12. A pharmaceutical composition for inhibiting the expression of a target gene in a mammal, wherein the pharmaceutical composition comprises at least one RNA molecule of claim 1, and a pharmaceutically acceptable carrier.

13. The pharmaceutical composition of claim 12, wherein the RNA molecule is comprised of only unmodified natural nucleotides.

14. The pharmaceutical composition of claim 12, wherein the length of the double-stranded part is from 8 to 50 nucleotides.

15. The pharmaceutical composition of claim 12, wherein the length of the double-stranded part is from 14 to 27 nucleotides, and at least one of the RNA strand contains a protruding 3' end of 1-5 nucleotides, wherein said RNA molecule can exert gene-specific RNA interference.

16. The pharmaceutical composition of claim 12, wherein said RNA molecule is stable in mammalian body fluids of a mammalian animal for a time longer than 10 minutes, 30 minutes, 1 hour, or 6 hours.

17. The pharmaceutical composition of claim 12, wherein 70% or 90% of said RNA molecule maintain integrity double-stranded structure after contacting with mammalian body fluids.

18. The RNA molecule of claim 1, wherein the content of CA/UG and/or UG/CA sequence is 0%; or the content of the combination of UA/UA and (CA/UG and/or UG/CA) sequence is not greater than 9%, 8%, or 6%, or is 0%.

* * * * *